(12) United States Patent
Lecomte et al.

(10) Patent No.: US 10,864,092 B2
(45) Date of Patent: Dec. 15, 2020

(54) OVERMOULD ATTACHMENTS FOR PROSTHETIC FOOT

(71) Applicant: Össur Iceland ehf, Reykjavik (IS)

(72) Inventors: Christophe Guy Lecomte, Reykjavík (IS); María Guðrún Sveinbjörnsdóttir, Mosfellsbær (IS); Ragnar Örn Gunnarsson, Reykjavík (IS)

(73) Assignee: Össur Iceland ehf, Reykjavik (IS)

( * ) Notice: Subject to any disclaimer, the term of this patent is extended or adjusted under 35 U.S.C. 154(b) by 31 days.

(21) Appl. No.: 15/675,116

(22) Filed: Aug. 11, 2017

(65) Prior Publication Data

US 2017/0333221 A1  Nov. 23, 2017

Related U.S. Application Data

(62) Division of application No. 14/174,654, filed on Feb. 6, 2014, now abandoned.
(Continued)

(51) Int. Cl.
*A61F 2/66* (2006.01)
*A61F 2/50* (2006.01)

(52) U.S. Cl.
CPC ........ *A61F 2/66* (2013.01); *A61F 2002/5001* (2013.01); *A61F 2002/503* (2013.01);
(Continued)

(58) Field of Classification Search
CPC ...... A61F 2/66; A61F 2/78; A61F 2002/5001; A61F 2002/5055; A61F 2002/6614;
(Continued)

(56) References Cited

U.S. PATENT DOCUMENTS 1,452,302 A * 4/1923 Loven .................. A41B 11/004
2/239
3,062,557 A  11/1962 Underwood et al.
(Continued)

FOREIGN PATENT DOCUMENTS

CN  1835721 A  9/2006
CN  101155557 A  4/2008
(Continued)

OTHER PUBLICATIONS

O'Donnell, Leslie. Daphne Hegreness: On the right track. O&P Edge Magazine. (Year: 2011).*
(Continued)

*Primary Examiner* — Christie L Bahena
(74) *Attorney, Agent, or Firm* — Knobbe, Martens, Olson & Bear, LLP

(57) ABSTRACT

An attachment for a prosthetic foot comprising an attachment surface that couples to the edges of a foot plate of a prosthetic foot and an outer surface that functionally or cosmetically alters the foot plate of the prosthetic foot in order to adapt the prosthetic foot to the needs of the user. In another embodiment, a toe attachment for a prosthetic foot comprising a cavity that can receive the toe end of an elongate foot element of a prosthetic foot, the toe attachment that can functionally or cosmetically alter the elongate foot element in order to adapt the prosthetic foot to the needs of the user. In yet another embodiment, a seal cover that can removably engage a prosthetic foot and a cosmetic cover for a prosthetic foot, resulting in a substantially watertight connection between the seal cover and the prosthesis and the seal cover and the cosmesis.

5 Claims, 38 Drawing Sheets

Related U.S. Application Data

(60) Provisional application No. 61/764,424, filed on Feb. 13, 2013.

(52) U.S. Cl.
CPC ............... *A61F 2002/5024* (2013.01); *A61F 2002/5027* (2013.01); *A61F 2002/5083* (2013.01); *A61F 2002/6621* (2013.01); *A61F 2002/6657* (2013.01)

(58) Field of Classification Search
CPC ...... A61F 2002/6628; A61F 2002/6635; A61F 2002/6642; A61F 2002/665; A61F 2002/6657; A61F 2002/6664; A61F 2002/6671; A61F 2002/6678; A61F 2002/6685; A61F 2002/6692
See application file for complete search history.

(56) References Cited

U.S. PATENT DOCUMENTS

| | | | |
|---|---|---|---|
| 5,653,767 | A | 8/1997 | Allen et al. |
| 5,653,768 | A * | 8/1997 | Kania .................. A61F 2/66 623/27 |
| 5,888,239 | A | 3/1999 | Wellershaus et al. |
| 6,071,313 | A | 6/2000 | Phillips |
| 6,165,228 | A | 12/2000 | Lindh |
| 6,596,029 | B1 | 7/2003 | Gramnäs |
| 6,811,571 | B1 | 11/2004 | Phillips |
| 7,310,894 | B1 | 12/2007 | Schwarzman et al. |
| 8,323,354 | B2 | 12/2012 | Bedard et al. |
| 8,535,390 | B1 | 9/2013 | Lecomte et al. |
| 2004/0054423 | A1 | 3/2004 | Martin |
| 2004/0059429 | A1 | 3/2004 | Amin et al. |
| 2005/0038524 | A1 | 2/2005 | Jonsson et al. |
| 2006/0167546 | A1 | 7/2006 | Bartlett |
| 2011/0054634 | A1 | 3/2011 | Bartlett |
| 2012/0179274 | A1 * | 7/2012 | Christensen .............. A61F 2/66 623/55 |
| 2012/0191220 | A1 | 7/2012 | Bedard et al. |
| 2012/0209406 | A1 | 8/2012 | Chen et al. |
| 2012/0271434 | A1 | 10/2012 | Friesen et al. |
| 2012/0283846 | A1 | 11/2012 | Janssen et al. |
| 2012/0303135 | A1 | 11/2012 | Vo |
| 2013/0024008 | A1 | 1/2013 | Treger et al. |
| 2014/0228974 | A1 | 8/2014 | Lecomte et al. |

FOREIGN PATENT DOCUMENTS

| | | | | |
|---|---|---|---|---|
| CN | 102665614 A | | 9/2012 | |
| GB | 2249939 A | * | 5/1992 | ............... A43B 5/06 |
| WO | WO 2008/091662 A1 | | 7/2008 | |
| WO | WO 2011066354 A2 | * | 6/2011 | ............... A61F 2/66 |
| WO | WO 2012/009319 A2 | | 1/2012 | |
| WO | WO 2012009319 A2 | * | 1/2012 | ............... A61F 2/66 |

OTHER PUBLICATIONS

International Search Report and Written Opinion for PCT/US2014/014939, dated Jun. 26, 2014 in 15 pages.
Ottobock 1A30 Greissinger Plus product; http://www.ottobock.com/cps/rde/xchg/ob_com_en/hs.xsl/1790.html; believed to be available before Feb. 13, 2013.
College Park Accent DP product; http://www.college-park.com/images/pdf/cpi-manual-accent-dp.pdf; believed to be available before Feb. 13, 2013.
Endolite. Endolite Running Blade-Paralympics London 201. Aug. 30, 201. Youtube.
Honeywell. Honeywell Material Provides Strength and Comfort for O&P Products. O&P Edge. Mar. 22, 2006.
Nike (1), (2), (3), (4). Nike Invents a "Shoe" for Athletes with Prosthetic Limbs. Co.Design. Feb. 2, 2012.
Thrive. Verified by the Wayback Machine, Feb. 3, 2012.
Triton. Ottobock. Verified by the Wayback Machine, Sep. 6, 2012.
EZ Trim. Slim and Trim. O&P Magazine. Oandp.com, Jun. 2004.
Catalyst. Trulife ad. www.trulife.com, date verified by wayback machine, Jan. 30, 2011.
Oandp.com. Listserve. Chris Johnson. Vaseline on Spectra Sock. Nov. 1998.
Supplemental Search Report from corresponding European Patent Application No. Ep 14751312, dated Dec. 1, 2015, in 3 pages.
Search Opinion from corresponding European Patent Application No. EP 14751312, dated Apr. 11, 2015, in 4 pages.
Office Action in corresponding Chinese Patent Application No. 201480019457.5, dated Jun. 2, 2016, in 12 pages.

* cited by examiner

OVERMOULD ATTACHMENTS FOR PROSTHETIC FOOT

CROSS-REFERENCE TO RELATED APPLICATIONS

This application is a divisional application of U.S. application Ser. No. 14/174,654, filed Feb. 6, 2014, which claims priority to U.S. Provisional Application No. 61/764,424 filed Feb. 13, 2013, which is hereby expressly incorporated in its entirety by reference herein and should be considered a part of this specification.

BACKGROUND

Field

Embodiments of the present invention relate to prosthetic feet and overmould attachments and cosmetic covers for prosthetic feet.

Description of the Related Art

Prosthetic feet of different designs are well known in the art. The various conventional designs have sought to solve various limitations associated with prosthetic feet. One limitation associated with prosthetic feet known in the art has to do with manufacturing prosthetic feet having foot plates with varying characteristics. Some of the possible variations of a foot plate include width, length, thickness, shape, and stiffness. Incorporating one or more of these variations into the design of a prosthesis can result in a prosthesis with characteristics that are desirable or beneficial for a particular user or a particular use. However, incorporating these variations directly into the foot plate during the manufacturing process can be expensive, time consuming and result in waste of the production materials.

Accordingly, there is a need for an improved design that is economically efficient to manufacture while still providing the advantages to the user of having variations in the foot plate.

Another limitation associated with prosthetic feet known in the art has to do with wear and tear on the prosthesis. Materials typically used in the art to produce prosthetic feet, such as carbon fiber, can be expensive and difficult to repair or replace. During the course of use of a prosthetic foot, normal wear and tear can result in undesirable cosmetic or structural damage to the foot plate or any other element of the prosthesis. Such damage can be very difficult or expensive to repair and can require that the entire foot plate of the prosthesis be replaced.

Accordingly, there is a need for an improved design that protects the foot plate from the damage associated with normal wear and tear and allows for a damaged element or portion of the prosthesis to be easily and economically repaired or replaced.

Yet another limitation associated with prosthetic feet known in the art has to do with water and/or debris, such as dirt, entering the cosmetic foot cover. This water and/or debris can be difficult to clean out from the cosmetic cover and can cause problems with the function of the cosmetic cover or prosthesis therein. On the other hand, sealing the opening of a cosmetic cover can limit the function of the ankle joint and make access for manipulation or adjustment of the ankle very difficult.

Accordingly, there is a need for an improved foot cover or foot cover attachment that can prevent water and/or debris from entering the foot cover, but that will still allow for easy adjustments and manipulation of the ankle and attachment or adaptors,

SUMMARY

In accordance with one embodiment disclosed herein, a prosthetic foot comprising at least one foot plate that can be coupled to an attachment is provided. The foot plate has a toe end, an ankle end, a toe surface or edge, an ankle surface or edge, medial and lateral side surfaces or edges, a top surface, and a bottom surface. The foot plate can be made of carbon fiber or any other material used in the art to manufacture foot plates for prosthetic feet. The foot plate can be generally straight, or it can be curved between the toe end and the ankle end such that the toe end is substantially horizontal while the ankle end is substantially vertical. The foot plate can be coupled to an attachment at the toe end, wherein the attachment extends at least partially along the length of the side surfaces from the toe end toward the ankle end. In some embodiments, the attachment extends all the way along the side surfaces wherein it is also coupled to the ankle surface. In embodiments in which the foot plate is curved and the attachment extends along the sides to at least the portion where the foot plate is curved, the portion of the attachment along the side surfaces will also curve to match the side surfaces. The foot plate can be coupled to an attachment that can extend at least partially over the top surface and/or at least partially over the bottom surface of the foot plate. In some embodiments, the prosthetic foot can have a heel plate connected to the bottom surface of the foot plate and extending away from the toe end of the foot plate.

The foot plate can be removably coupled to the attachment. The foot plate can be coupled to the attachment using at least one clip mechanism, a series of clips, glue or epoxy, magnetic force, elastic properties of the attachment (e.g., press-fit connection) and/or any other coupling mechanism known in the art. In some embodiments, the attachment is not coupled with or in contact with the heel plate.

The attachment can alter the shape of the foot plate such that the altered shape of the foot plate is more similar to the shape of a natural human foot. Alternatively, the altered shape of the foot plate can provide the prosthetic foot and its user with other functional or cosmetic benefits. For example, the altered shape of the foot plate can aid in fitting the prosthesis into a foot cover or shoe.

In some embodiments, the foot plate has a lengthwise split beginning at the toe end of the foot plate and traversing at least part of the length of the foot plate that divides the foot plate resulting in a medial portion and a lateral portion. In some embodiments, the lengthwise split does not span the entire length of the foot plate, and thus the medial and lateral portions join into a singular foot plate at some point between the toe end and the ankle end of the foot plate. In some embodiments, the attachment will have a corresponding split at the toe end. The split in the foot plate and the attachment allow the medial and lateral portions to flex at least somewhat independently, improving functional properties of the prosthetic foot during rollover.

In accordance with another embodiment disclosed herein, a prosthetic foot with a foot plate that can receive a coupleable toe attachment at the toe end of the foot plate is provided. The foot plate has a toe end, an ankle end, a toe surface, an ankle surface, medial and lateral side surfaces, a top surface, and a bottom surface. The foot plate can be made of carbon fiber or any other material used in the art to manufacture foot plates for prosthetic feet. The foot plate can be straight, or it can be curved between the toe end and the ankle end such that the toe end is substantially horizontal while the ankle end is substantially vertical. The ankle end of the foot plate can attach to an adaptor or a residual limb. The foot plate has sides that are substantially straight resulting in a more economical and efficient manufacturing process. The foot plate is manufactured to a standard size resulting in a more economical and efficient manufacturing process.

The foot plate can be coupled at the toe end to a toe attachment that extends at least partially over the top surface and at least partially over the bottom surface of the foot plate. The foot plate can be removably coupled to the toe attachment, the toe attachment having a cavity that can receive the toe end of the foot plate. The toe attachment alters the shape of the foot plate such that the altered shape of the foot plate is more similar to the shape of a natural human foot. The altered shape of the foot plate can aid in fitting the prosthesis into a foot cover or shoe.

In accordance with another embodiment, an overmould attachment that is coupleable to a foot plate of a prosthetic foot is provided. The overmould attachment is coupled to the toe end or toe surface of the foot plate, and at least partially along the medial and lateral side surfaces of the foot plate. In some embodiments, the attachment extends along the entire length of the side surfaces and at least partially onto an ankle surface of the foot plate. The attachment is removably coupleable to a prosthetic foot. The attachment is made out of polymer or a plastic-like material or a compressible material. In other embodiments, the attachment is made of any material used in the art. The attachment can alter the stiffness or thickness characteristics of the foot plate.

The attachment alters the cosmetic appearance of the prosthetic foot and protects the prosthetic foot from wear and tear. The attachment can be coupled to a prosthetic foot without altering any fit adjustments made to the prosthetic foot. In some embodiments, the attachment alters the shape of the foot plate such that the altered shape of the foot plate is more similar to the shape of a natural human foot. Alternatively, the altered shape of the foot plate can provide the prosthetic foot and the user with other functional or cosmetic benefits. For example, the altered shape of the foot plate can aid in fitting the prosthesis into a foot cover or shoe.

In accordance with another embodiment disclosed herein, an overmould attachment that includes an extended portion at the toe end of the foot plate is provided. The extended portion includes a cutout section resulting in a medial lobe and a lateral lobe. The cutout is generally U-shaped. The respective widths of the medial and lateral lobes result in a stiffness for the medial and lateral lobes, wherein varying the widths of the medial and lateral lobes results in varying the stiffness of the medial and lateral lobes. The characteristics of the medial and lateral lobes can result in improved rollover during use of the prosthetic coupled to the attachment. Additionally, the extended portion can aid in fitting the prosthesis into a foot cover or shoe.

In accordance with another embodiment disclosed herein, a prosthetic foot is provided. The prosthetic foot comprises an elongate foot member having a distal toe end with a distal toe surface, a proximal ankle end, and medial and lateral surfaces extending along a length of the elongate foot member. The prosthetic foot also comprises an attachment member coupleable to the elongate foot member along an entire length of the attachment member. The attachment member is configured to attach to at least the distal toe surface and the medial and lateral surfaces of the elongate foot member to alter a shape of the prosthetic foot by increasing one or both of a width and a length of at least a portion of the elongate foot member.

In accordance with another embodiment disclosed herein, a prosthetic foot is provided. The prosthetic foot comprises an elongate foot member having a distal toe end with a distal toe surface, a proximal ankle end, and medial and lateral surfaces extending along a length of the elongate foot member. The prosthetic foot also comprises an attachment member coupleable to the elongate foot member along the entire length of the attachment member. The attachment member is configured to attach to at least the distal toe surface and the medial and lateral surfaces of the elongate foot member and can alter the shape of the prosthetic foot by increasing one or both of a width and a length of at least a portion of the elongate foot member. The attachment member has a side profile that matches a profile of the elongate foot member.

In accordance with yet another embodiment disclosed herein, a coupleable toe attachment for use with a prosthetic foot is provided. The toe attachment is removably coupleable to a prosthetic foot. The toe attachment further includes a cutout section that divides the top surface and bottom surface into a medial lobe and a lateral lobe. The cutout is generally U-shaped. The cutout, resulting in a medial and lateral lobe, gives the toe attachment a more anatomical or a "sandal toe" appearance. The respective widths of the medial and lateral lobes result in a stiffness for the medial and lateral lobes, wherein varying the widths of the medial and lateral lobes results in varying the stiffness of the medial and lateral lobes. Additionally, the toe attachment can aid in fitting the prosthesis into a foot cover or shoe.

The toe attachment can have a cavity that can receive the toe end of foot plate of a prosthetic foot, such that the toe end of a foot plate fits inside the cavity. In some embodiments, at least part of the cavity extends all the way through the toe attachment. The toe attachment is coupled to a foot plate of a prosthetic foot using clips, glue or epoxy, magnetic force, and/or any other coupling mechanism known in the art.

In accordance with another embodiment disclosed herein, a prosthetic foot is provided. The prosthetic foot comprises an elongate foot member having a toe end and an ankle end. The prosthetic foot also comprises a toe attachment removably coupleable solely to the toe end of the elongate foot member. The toe attachment has a top surface, a bottom surface, a distal end, a proximal end, the toe attachment defining a slot therein and having a length shorter than a length of the elongate foot member. The slot in the toe attachment extends from the top surface to the bottom surface defining a medial lobe and a lateral lobe of the toe attachment. The slot is configured to removably receive a strap of a sandal when said sandal is coupled to the prosthetic foot.

In accordance with another embodiment disclosed herein, a seal cover for a cosmetic cover for a prosthetic foot is provided. Viewed from above, the seal cover generally has the shape of the cross-section of a human ankle or of the opening of a cosmetic cover for a prosthetic foot. The seal cover has an outer portion and an inner portion. The inner portion and the outer portion are made of different materials. The outer portion is a frame made of a plastic or plastic-like material. The inner portion is a membrane made of an elastic or flexible material. The top surface of the outer portion is substantially flat. The bottom surface can have two concentric lips that run substantially parallel to the perimeter of the outer surface that can removably engage the opening of a cosmetic cover for a prosthetic foot after a prosthetic foot has been inserted into the cosmetic cover, creating a substantially watertight connection between the outer portion and the cosmetic cover.

The inner portion can include a membrane made of a flexible material, such as rubber or elastic, and has a circular O-ring opening that can engage a pyramid adaptor or foot plate or shank or pylon of a prosthetic foot system, creating a substantially watertight connection between the inner portion and the prosthetic foot system. In some embodiments, a collar adaptor can be placed on the prosthetic foot system that has a groove to receive the circular opening of the inner portion of the seal cover.

In accordance with another embodiment disclosed herein, a seal cover for a cosmetic cover for a prosthetic foot. Viewed from above, the seal cover generally has the shape of the cross-section of a human ankle or of the opening of a cosmetic cover for a prosthetic foot. The seal has an outer portion and an inner portion. The inner portion and the outer portion are made of different materials. The outer portion is a frame made of a plastic or plastic-like material. The inner portion is a membrane made of an elastic or flexible material. The top surface of the outer portion is substantially flat. The bottom surface of the outer portion of the seal cover engages the rim at the opening of the cosmetic cover after a prosthetic foot has been inserted into the cosmetic cover using a series of hooked protrusions or teeth that can removably engage complementary cavities in the rim of the cosmetic cover in order to facilitate the engagement of the seal cover to the cosmetic cover. Additionally, glue or epoxy can be used along the points of attachment to further improve engagement of the seal cover to the cosmetic cover.

The inner portion is a membrane made of a flexible material, such as rubber or elastic, and has a circular O-ring opening that can engage a pyramid adaptor or foot plate or shank or pylon of a prosthetic foot system, creating a substantially watertight connection between the inner portion and the prosthetic foot system. In some embodiments, a collar adaptor can be placed on the prosthetic foot system that has a groove to receive the circular opening of the inner portion of the seal cover.

DETAILED DESCRIPTION

Figure 1:
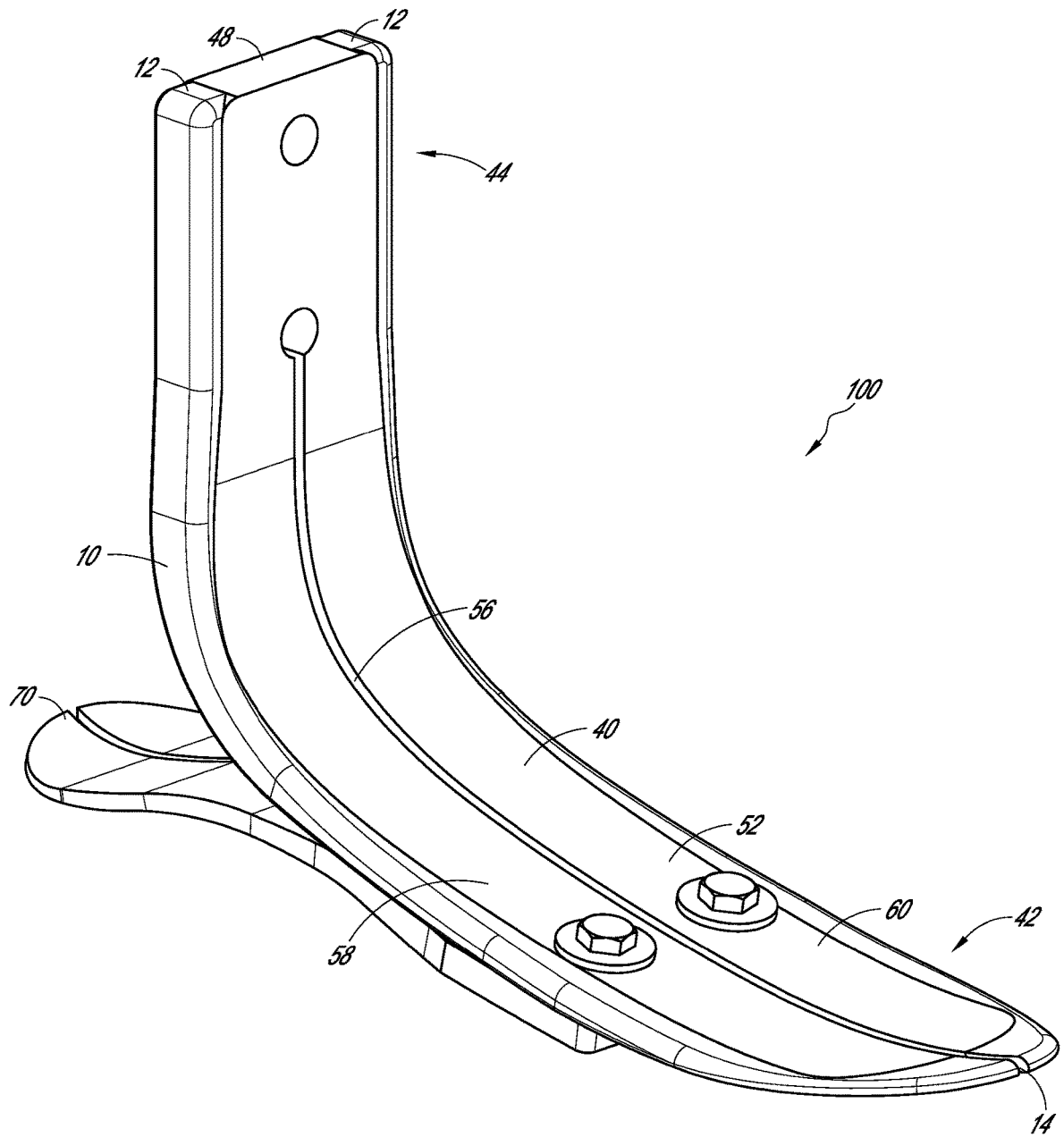
FIG. 1 is a partial side, top and front profile view of one embodiment of an overmould attachment coupled to a prosthetic foot.
Figure 2:
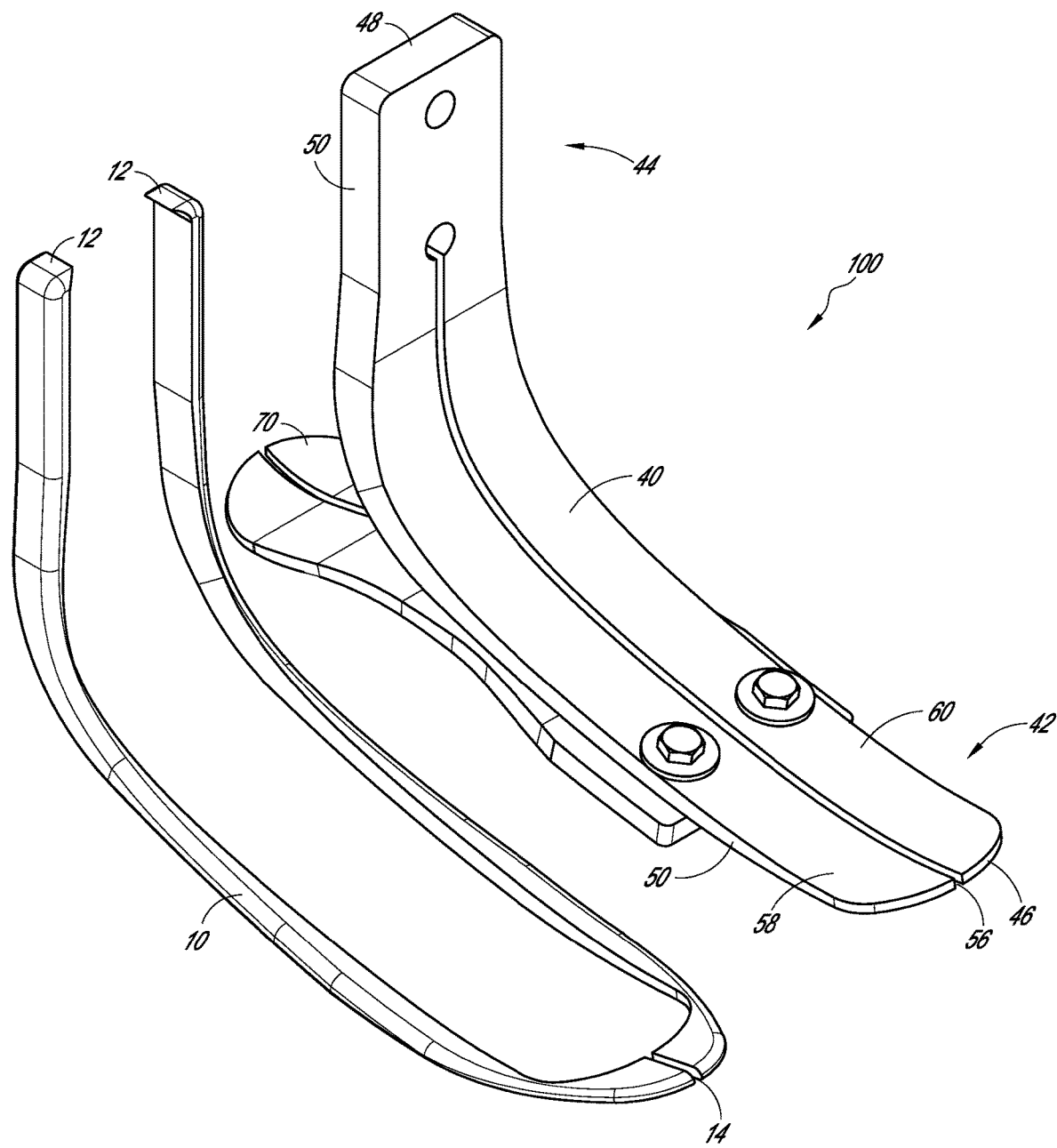
FIG. 2 is a partial side, top and front profile view of the prosthetic foot in FIG. 1 that can be coupled to an overmould attachment and an overmould attachment that can be coupled to a prosthetic foot, with the prosthetic foot and the overmould separated.
Figure 3:
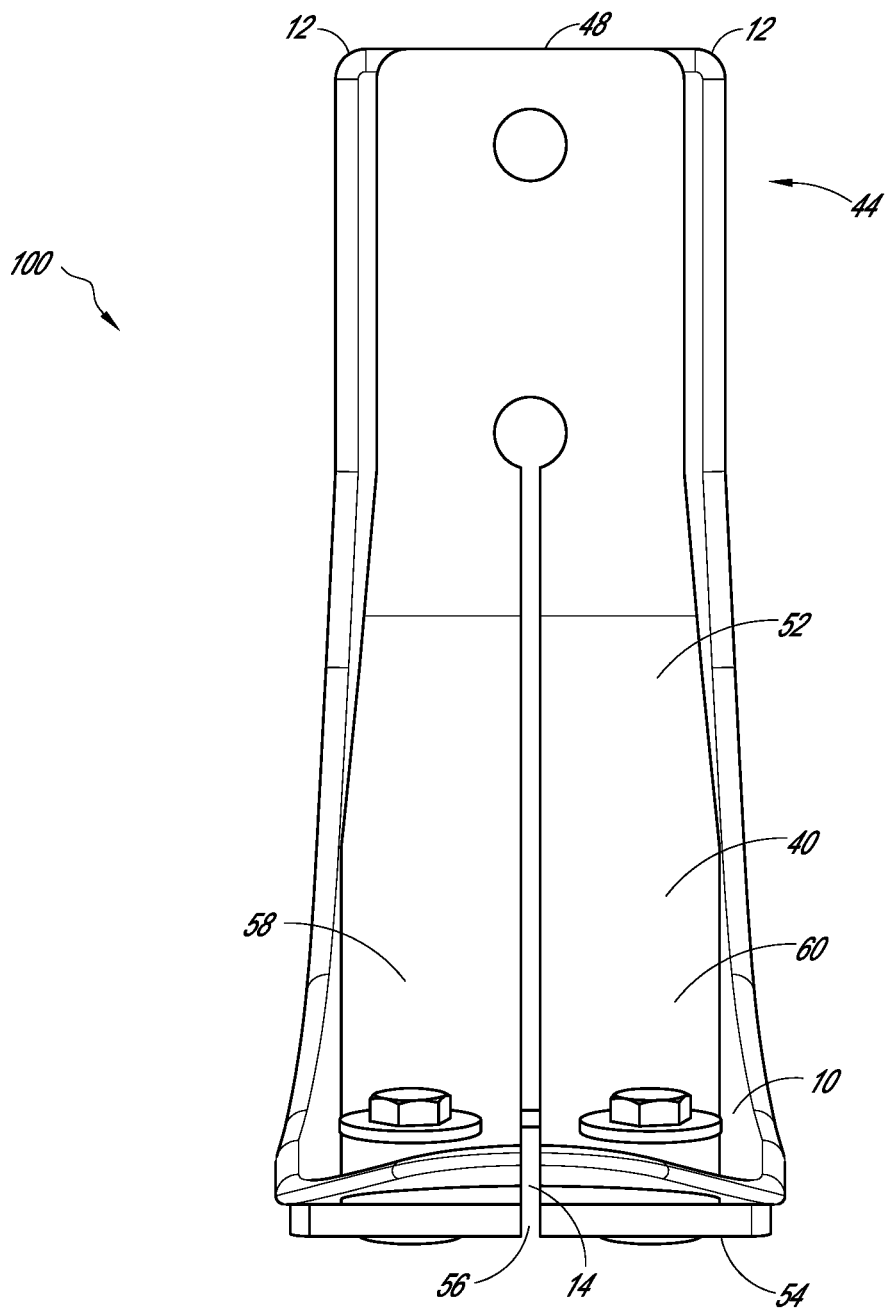
FIG. 3 is a front profile view of the overmould attachment coupled to the prosthetic foot of FIG. 1.
Figure 4:
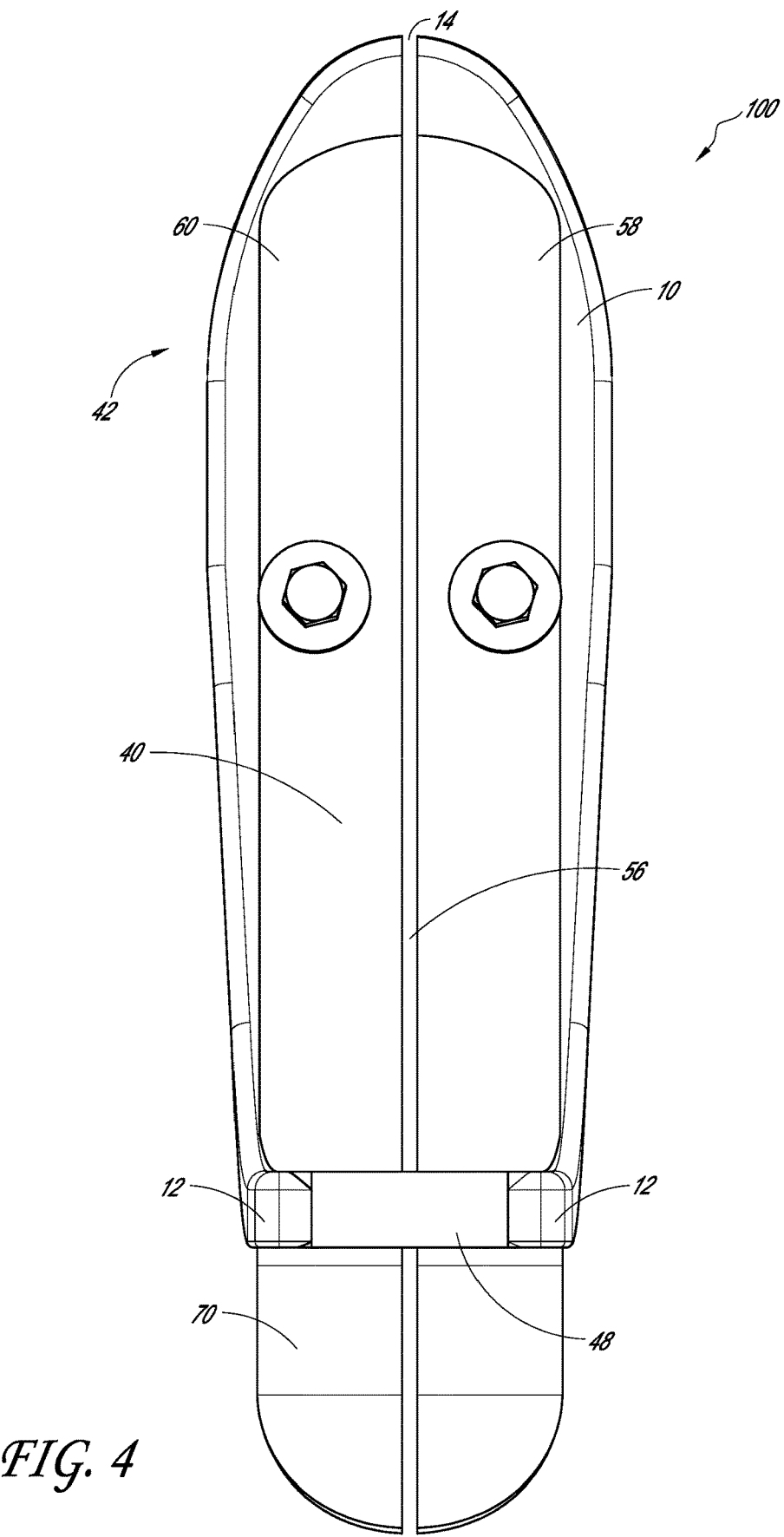
FIG. 4 is a top plan view of the overmould attachment coupled to the prosthetic foot of FIG. 1.
Figure 5:
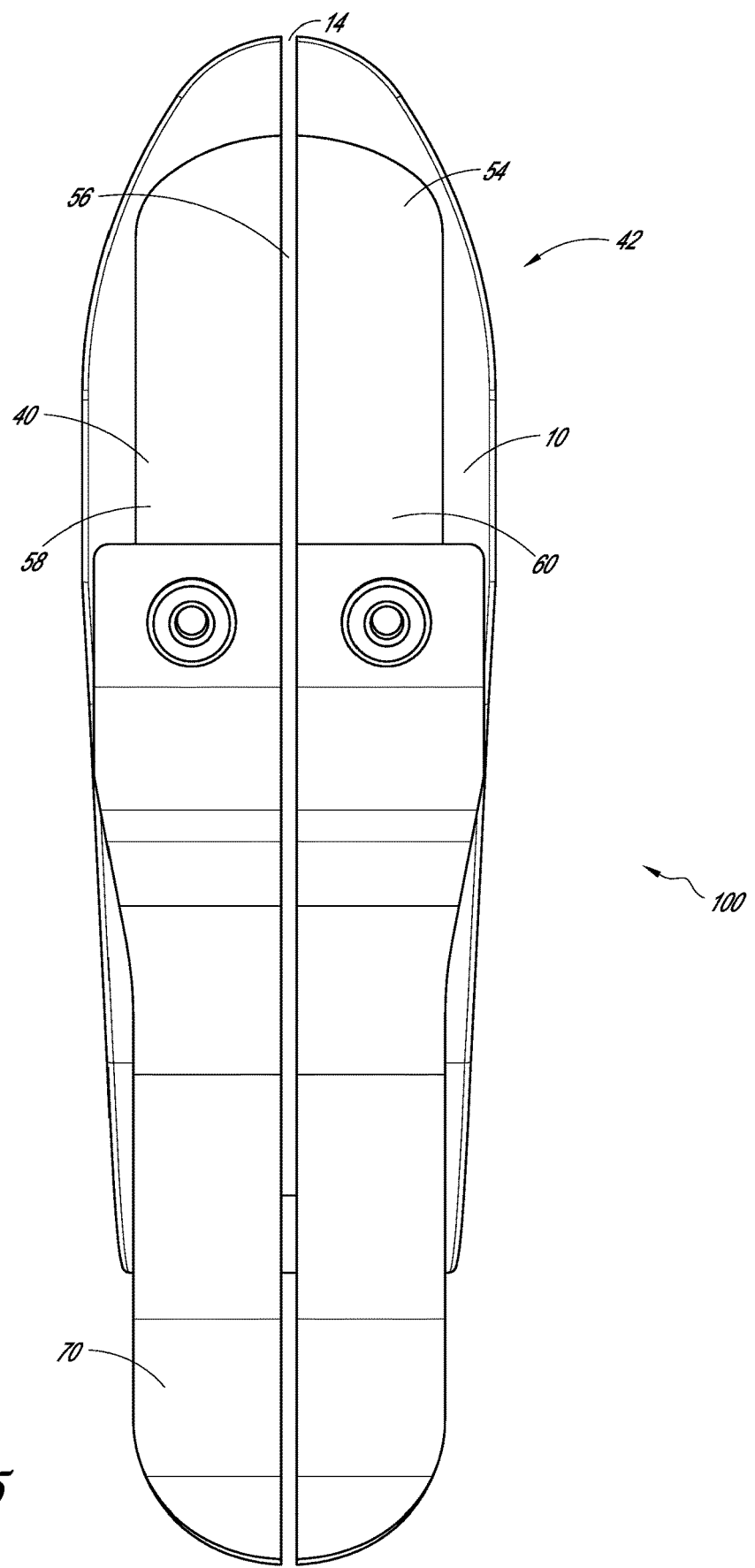
FIG. 5 is a bottom plan view of the overmould attachment coupled to the prosthetic foot of FIG. 1.
Figure 6:
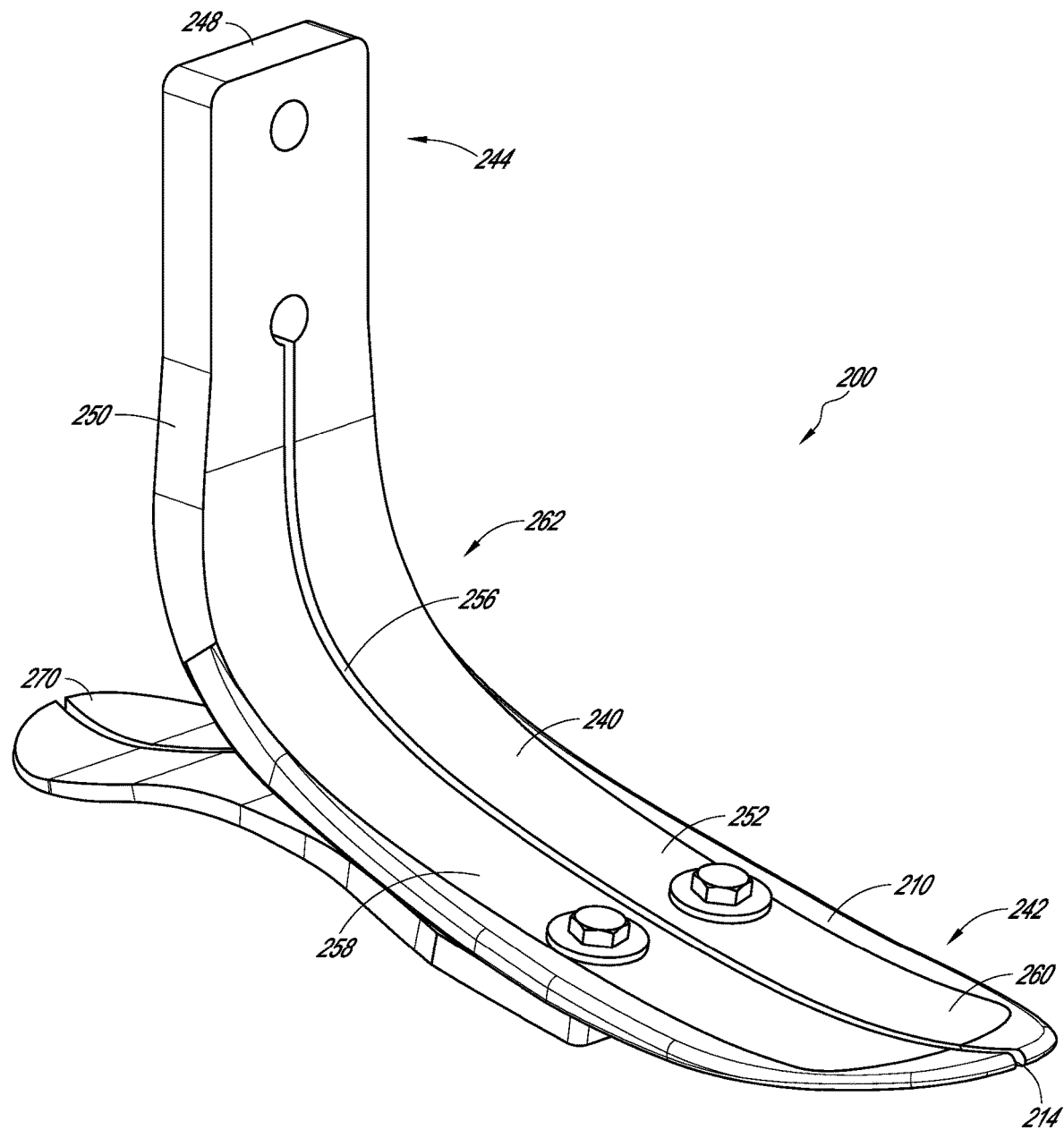
FIG. 6 is a partial side, top and front profile view of another embodiment of an overmould attachment coupled to a prosthetic foot.
Figure 7:
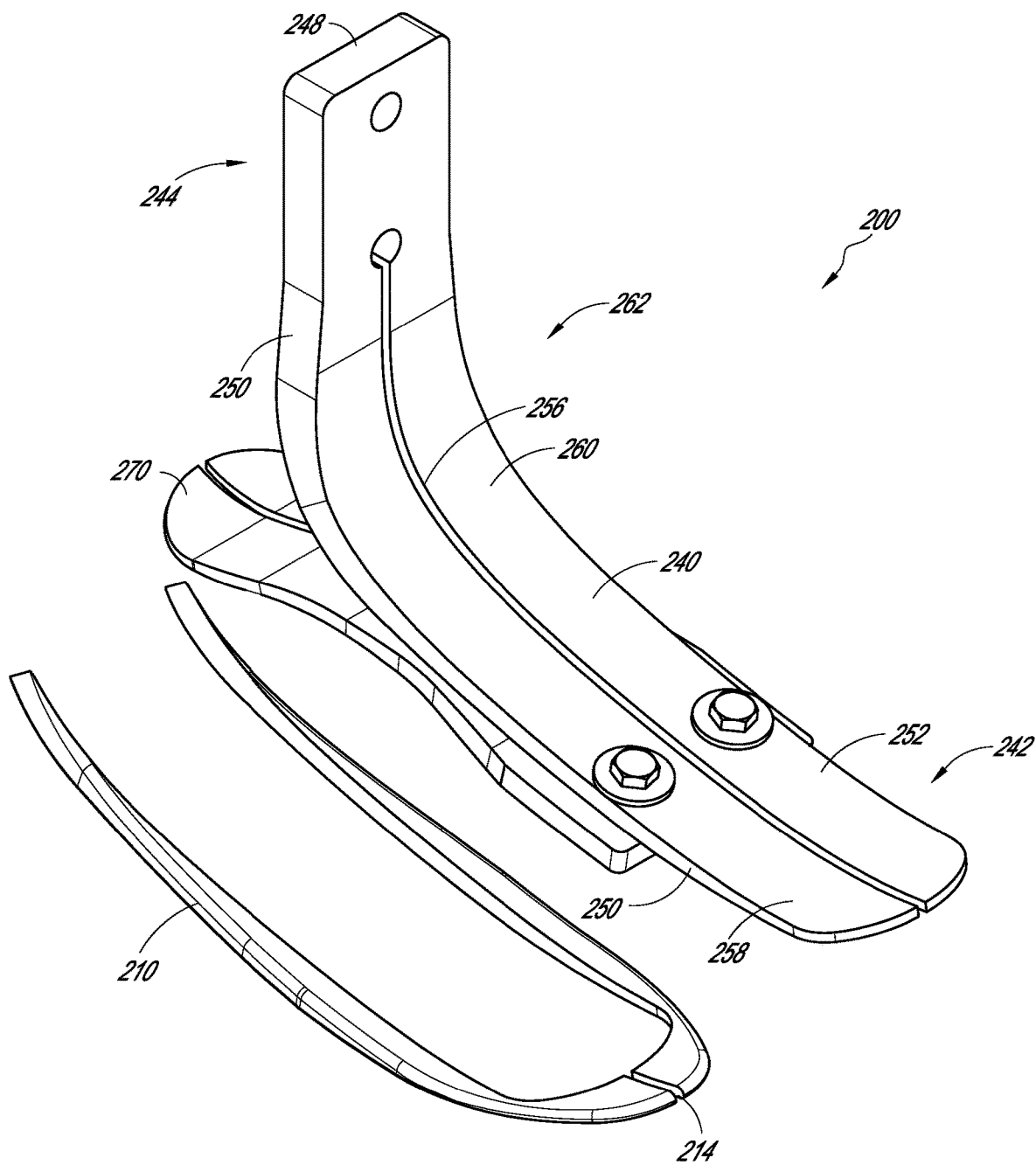
FIG. 7 is a partial side, top and front profile view of the prosthetic foot in FIG. 6 that can be coupled to an overmould attachment and an overmould attachment that can be coupled to a prosthetic foot, with the prosthetic foot and the overmould separated.
Figure 8:
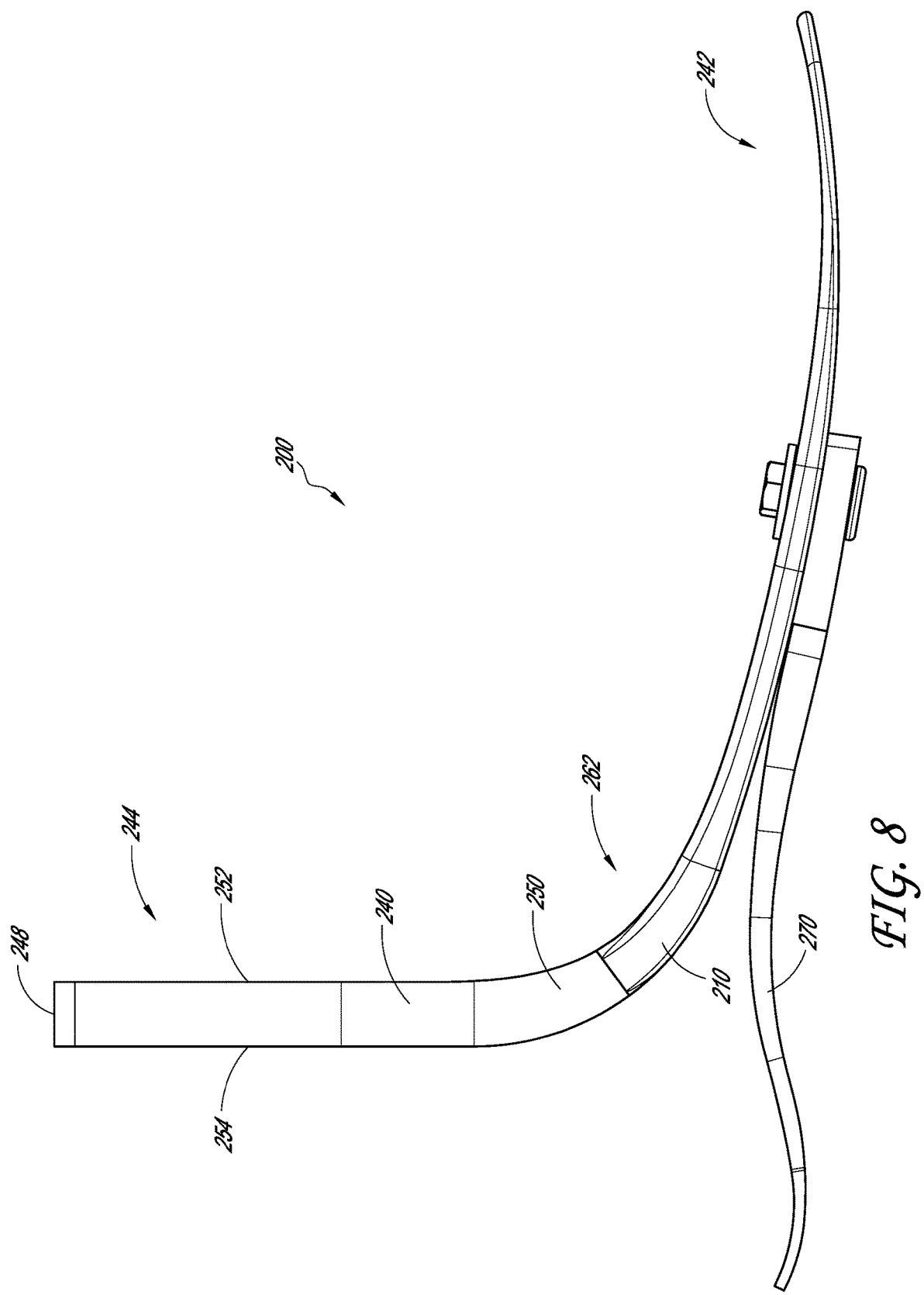
FIG. 8 is a side profile view of the overmould attachment coupled to the prosthetic foot of FIG. 6.

FIGS. 1-5 illustrate one embodiment of an overmould attachment 10 coupleable to a foot plate 40 of a prosthetic foot 100. The foot plate 40 generally can have a toe end 42 and an ankle end 44, as well as a toe surface or edge 46, an ankle surface or edge 48, and medial and lateral side surfaces or edges 50 extending from the toe surface 46 to the ankle surface 48. In one embodiment, the medial and/or lateral side surfaces or edges 50 extend generally linearly (e.g., do not curve outward in a transverse direction to the longitudinal axis of the foot 100), or the foot plate 40 is generally planar, between the toe end 42 and the ankle end 44 along at least a portion of their length. In another embodiment, the medial and or lateral side surfaces or edges 50 extend in a generally curved manner (e.g., curved in the medial-lateral direction and/or curved in the anterior-posterior direction) along at least a portion of their length between the toe end 42 and the ankle end 44. The foot plate 40 can also have a top surface 52 and a bottom surface 54 opposite the top surface 52. In some embodiments, the overmould attachment 10 is coupled to at least the toe surface 46 of the foot plate 40 of the prosthetic foot 100. In one embodiment, the overmould attachment 10 can be removably coupled to the foot plate 40 of the prosthetic foot 100. In some embodiments, as seen in FIG. 1, the overmould attachment 10 is coupled to the toe surface 46 and all along the entire length of the side surfaces 50 of the foot plate 40. In some embodiments, as shown in FIGS. 1, 3 and 4, at the ankle surface 48 of the foot plate 40, the overmould attachment 10 has portions 12 that extend at least partially over the ankle surface 48 of the foot plate 40. In some embodiments, the portions 12 of the overmould attachment 10 that extend at least partially over the ankle surface 48 help to couple the overmould attachment 10 to the foot plate 40. In some embodiments, the overmould attachment 10 extends at least partially over the top surface 52 of the foot plate and at least partially over the bottom surface 54 of the foot plate. In some embodiments, the overmould attachment 10 extends at least partially over the top surface 52 of the foot plate. In some embodiments, the overmould attachment 10 extends at least partially over the bottom surface 54 of the foot plate. In some embodiments, the prosthetic foot 100 can have a heel plate 70 disposed below (e.g., coupled to) the bottom surface 54 of the foot plate 40, extending away from the toe end 42. In one embodiment, the overmould attachment 10 is not coupled to the heel plate 70. In some embodiments, the overmould attachment 10 does not contact the heel plate 70.

In some embodiments, the foot plate 40 has a lengthwise split 56, beginning at the toe end 42 of the foot plate and extending at least part of the length of the foot plate 40, that divides the foot plate 40, resulting in a medial portion 58 and a lateral portion 60. In some embodiments, the lengthwise split 56 does not span the entire length of the foot plate 40, resulting in an undivided foot plate at the ankle end 44 of the foot plate 40. In some embodiments, the overmould attachment 10 will have a corresponding split 14 at the toe end 42. The splits 56 and 14 in the foot plate 40 and the overmould attachment 10 allow the medial and lateral portions 58 and 60 to flex at least somewhat independently, improving functional properties of the prosthetic foot during rollover or during use on different surfaces (e.g., on uneven terrain).

In one embodiment, as shown in FIG. 4, the overmould attachment 10 advantageously changes the shape of the foot plate 40. In some embodiments, the overmould attachment 10 changes the width of the foot plate 40. In some embodiments, the overmould attachment 10 changes the length of the foot plate 40. In some embodiments, the overmould attachment 10 advantageously changes the shape of the foot plate 40 to make it more like the shape of a natural human foot (e.g., to include a sandal toe slot). In some embodiments, the overmould attachment 10 advantageously changes the shape of the foot plate 40 to improve stability characteristics of the prosthetic foot 100. In some embodiments, the overmould attachment 10 advantageously changes the shape of the prosthetic foot 100 to improve functional characteristics of the prosthetic foot 100 during rollover. In some embodiments, the altered shape of the foot plate 40 allows the prosthetic foot 100 to be used with a shoe or other footwear without needing a cosmetic cover over.

In one embodiment, the overmould attachment 10 shown in FIGS. 1-5 removably couples to a foot plate 40 of a prosthetic foot 100. In some embodiments, the overmould attachment 10 is coupled or removably coupled to the foot plate 40 using at least one clip mechanism. In some embodiments, the overmould attachment 10 is coupled or removably coupled to the foot plate 40 using a series of clips. In other embodiments, the overmould attachment 10 is coupled or removably coupled to the foot plate 40 using glue or epoxy. In other embodiments, the overmould attachment 10 is coupled or removably coupled to the foot plate 40 using magnetic force. In other embodiments, the overmould attachment 10 is coupled to the foot plate 40 using a series of complementary magnets located at corresponding locations of the overmould attachment 10 and the foot plate 40. In still other embodiments, the overmould attachment 10 is coupled to the foot plate 40 using elastic properties of at least one part of the overmould attachment 10. In some embodiments, the overmould attachment 10 is coupled to the foot plate 40 using any method of coupling known in the art. In some embodiments, the overmould attachment 10 is coupled to the foot plate 40 using any combination of any of the aforementioned coupling mechanisms.

In some embodiments, the overmould attachment 10 is made of a polymer or plastic-like material or a compressible material. In some embodiments, the overmould attachment 10 is the same stiffness as the foot plate 40. In some embodiments, the overmould attachment 10 is cheaper and easier to manufacture than the foot plate 40. In some embodiments, the overmould attachment 10 protects the foot plate 40 of the prosthetic foot 100 from damage due to everyday wear and tear.

FIGS. 6-9 illustrate another embodiment of an overmould attachment 210 coupleable to a foot plate 240 of a prosthetic foot 200. The foot plate 240 generally can have a toe end 242 and an ankle end 244, as well as a toe surface or edge 246, an ankle surface or edge 248, and medial and lateral side surfaces or edges 250 extending from the toe surface 246 to the ankle surface 248. In one embodiment, the medial and/or lateral side surfaces or edges 250 extend generally linearly between the toe end 242 and the ankle end 244 along at least a portion of their length. In another embodiment, the medial and or lateral side surfaces or edges 250 extend in a generally curved manner along at least a portion of their length between the toe end 242 and the ankle end 244. The foot plate 240 can also have a top surface 252 and a bottom surface 254 opposite the top surface 252. In this embodiment, the overmould attachment 210 is coupled to the toe surface 246 of the foot plate 240 and along the side surfaces 250 of the foot plate 240 until about the portion 262 of the foot plate 240 where the foot plate 240 curves. In some embodiments, the overmould attachment 210 would extend along the side surfaces 250 of the foot plate 240 past the curved portion 262, with the overmould attachment 210 curving to match the curve of the side surfaces 250. In other embodiments, the overmould attachment would extend along the side surfaces 250 of the foot plate and stop before the curved portion 262. In some embodiments, the overmould attachment 210 extends at least partially over the top surface 252 of the foot plate 240 and at least partially over the bottom surface 254 of the foot plate 240. In some embodiments, the overmould attachment 210 extends at least partially over the top surface 252 of the foot plate 240. In some embodiments, the overmould attachment 210 extends at least partially over the bottom surface 254 of the foot plate 240. In some embodiments, the prosthetic foot 200 can have a heel plate 270 disposed below (e.g., coupled to) the bottom surface 254 of the foot plate 240, extending away from the toe end 242. In one embodiment, the overmould attachment 10 is not coupled to the heel plate 270. In some embodiments, the overmould attachment 10 does not contact the heel plate 270.

In some embodiments, the foot plate 240 has a lengthwise split 256, beginning at the toe end 242 of the foot plate and extending at least part of the length of the foot plate 240, that divides the foot plate 240, resulting in a medial portion 258 and a lateral portion 260. In some embodiments, the lengthwise split 256 does not span the entire length of the foot plate, resulting in an undivided foot plate at the ankle end 244 of the foot plate 240. In some embodiments, the attachment 210 will have a corresponding split 214 at the toe end 242. The splits 256 and 214 in the foot plate 240 and the overmould attachment 210 allow the medial and lateral portions 258 and 260 to flex at least somewhat independently, improving functional properties of the prosthetic foot during rollover and to accommodate use of the foot on different terrain.

Figure 9:
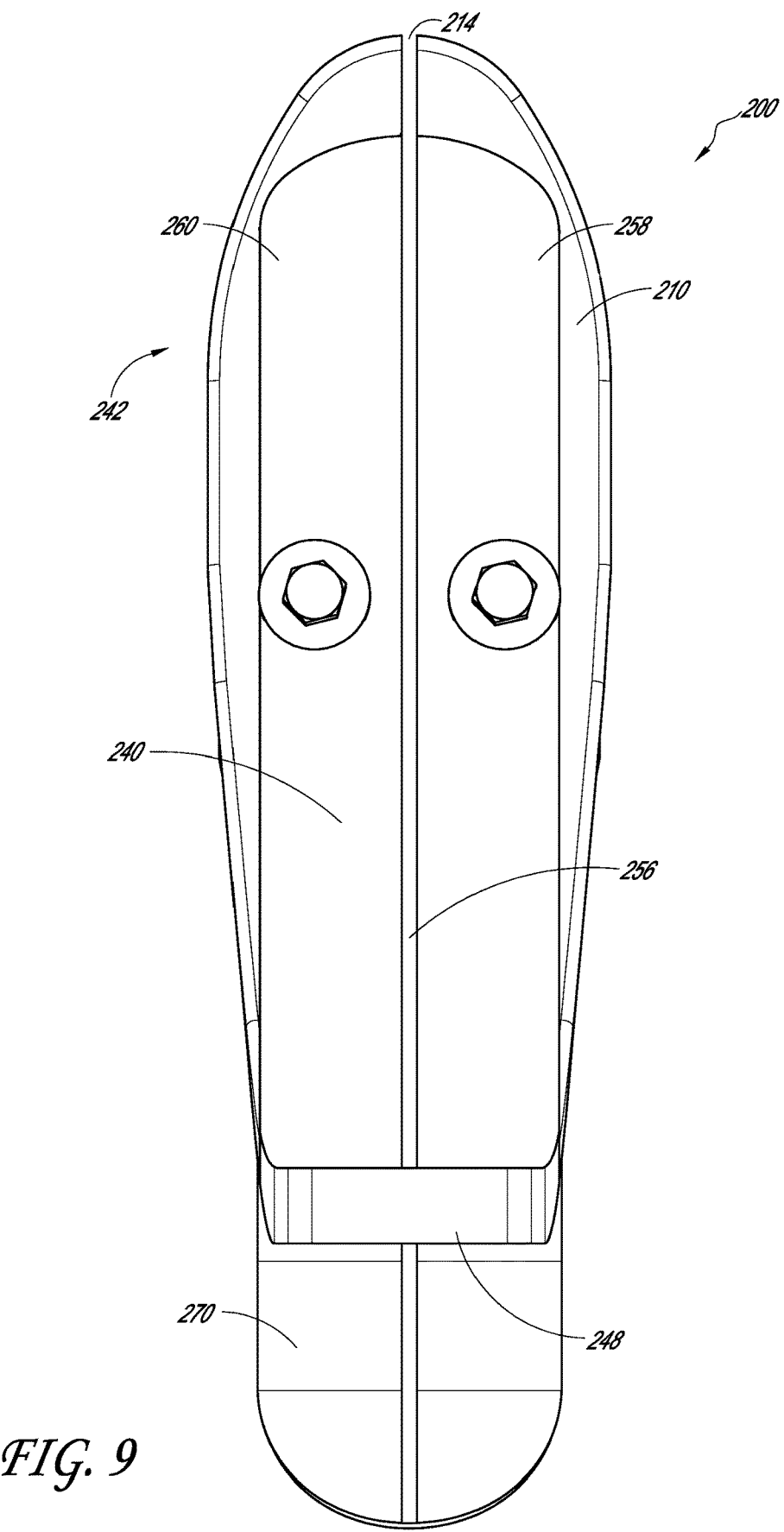
FIG. 9 is a top plan view of the overmould attachment coupled to the prosthetic foot of FIG. 6.

In one embodiment, as seen in FIG. 9, the overmould attachment 210 advantageously changes the shape of the foot plate 240. In some embodiments, the overmould attachment 210 changes the width of the foot plate 240. In some embodiments, the overmould attachment 210 changes the length of the foot plate 240. In some embodiments, the overmould attachment 210 advantageously changes the shape (e.g., contour) of the foot plate 240 to make it more like the shape of a natural human foot (e.g., to include a sandal toe slot). In some embodiments, the overmould attachment 210 advantageously changes the shape of the foot plate 240 to improve stability characteristics of the prosthetic foot 200 (e.g., by making the foot wider). In some embodiments, the overmould attachment 210 advantageously changes the shape of the foot plate 240 to improve functional characteristics of the prosthetic foot 200 during rollover. In some embodiments, the altered shape of the foot plate 240 allows the prosthetic foot 200 to be used with a shoe or other footwear without needing a cosmetic cover over.

In one embodiment, the overmould attachment 210 shown in FIGS. 6-9 can be removably coupled to a foot plate 240 of a prosthetic foot 200. In some embodiments, the overmould attachment 210 is coupled or removably coupled to the foot plate 240 using at least one clip mechanism. In some embodiments, the overmould attachment 210 is coupled or removably coupled to the foot plate 240 using a series of clips. In other embodiments, the overmould attachment 210 is coupled or removably coupled to the foot plate 240 using glue or epoxy. In other embodiments, the overmould attachment 210 is coupled or removably coupled to the foot plate 240 using magnetic force. In other embodiments, the overmould attachment 210 is coupled to the foot plate 240 using a series of complementary magnets located at corresponding locations of the overmould attachment 210 and the foot plate 240. In still other embodiments, the overmould attachment 210 is coupled to the foot plate 240 using elastic properties of at least one part of the overmould attachment 210. In some embodiments, the overmould attachment 210 is coupled to the foot plate 240 using any method of coupling known in the art. In some embodiments, the overmould attachment 210 is coupled to the foot plate 240 using any combination of any of the aforementioned coupling mechanisms.

In some embodiments, the overmould attachment 210 is made of a polymer or plastic-like material or a compressible material. In some embodiments, the overmould attachment 210 is the same stiffness as the foot plate 240. In some embodiments, the overmould attachment 210 is cheaper and easier to manufacture than the foot plate 240. In some embodiments, the overmould attachment 210 protects the foot plate 240 of the prosthetic foot 200 from damage due to everyday wear and tear.

Figure 10:
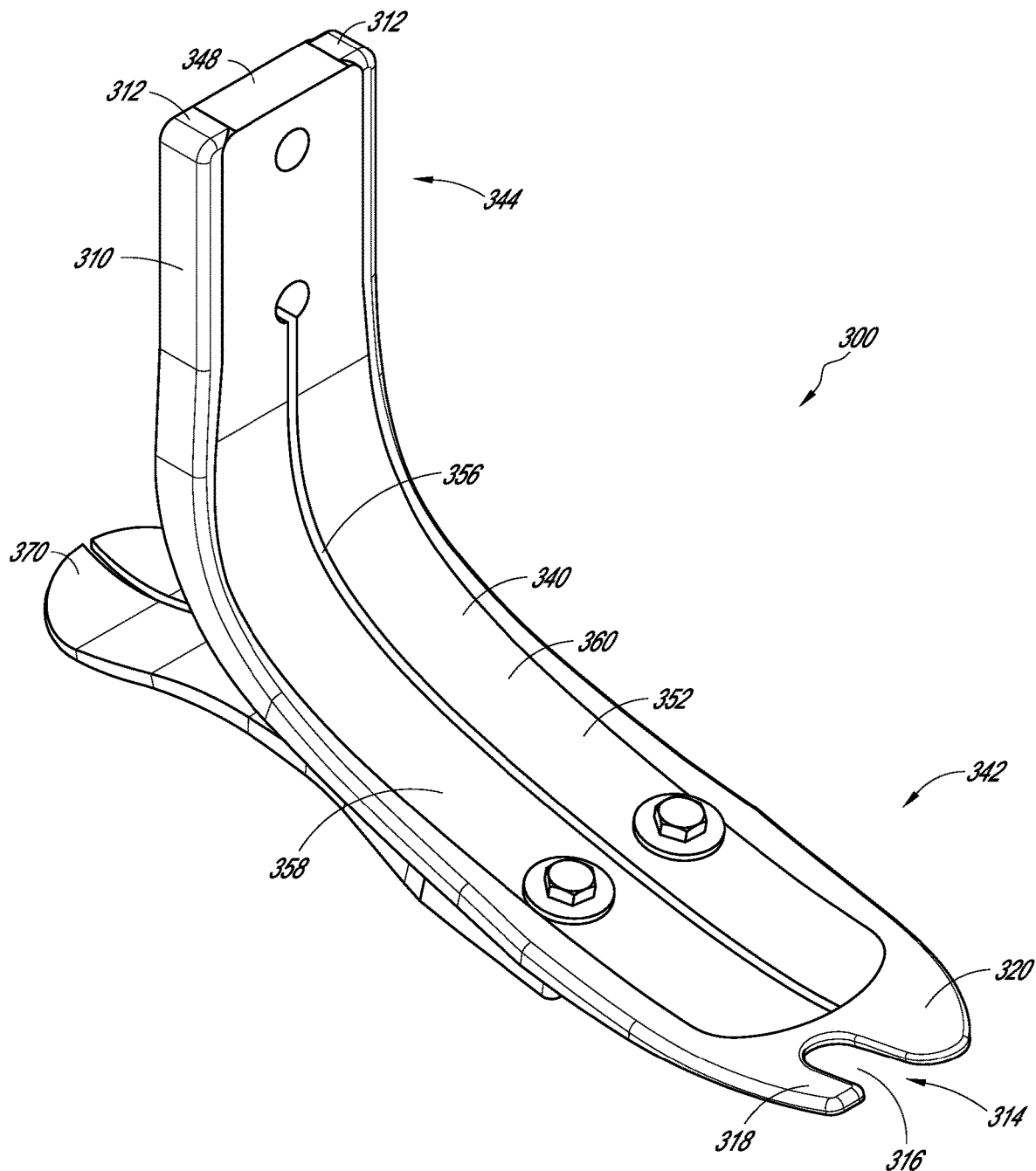
FIG. 10 is a partial side, top and front profile view of yet another embodiment of an overmould attachment coupled to a prosthetic foot.
Figure 11:
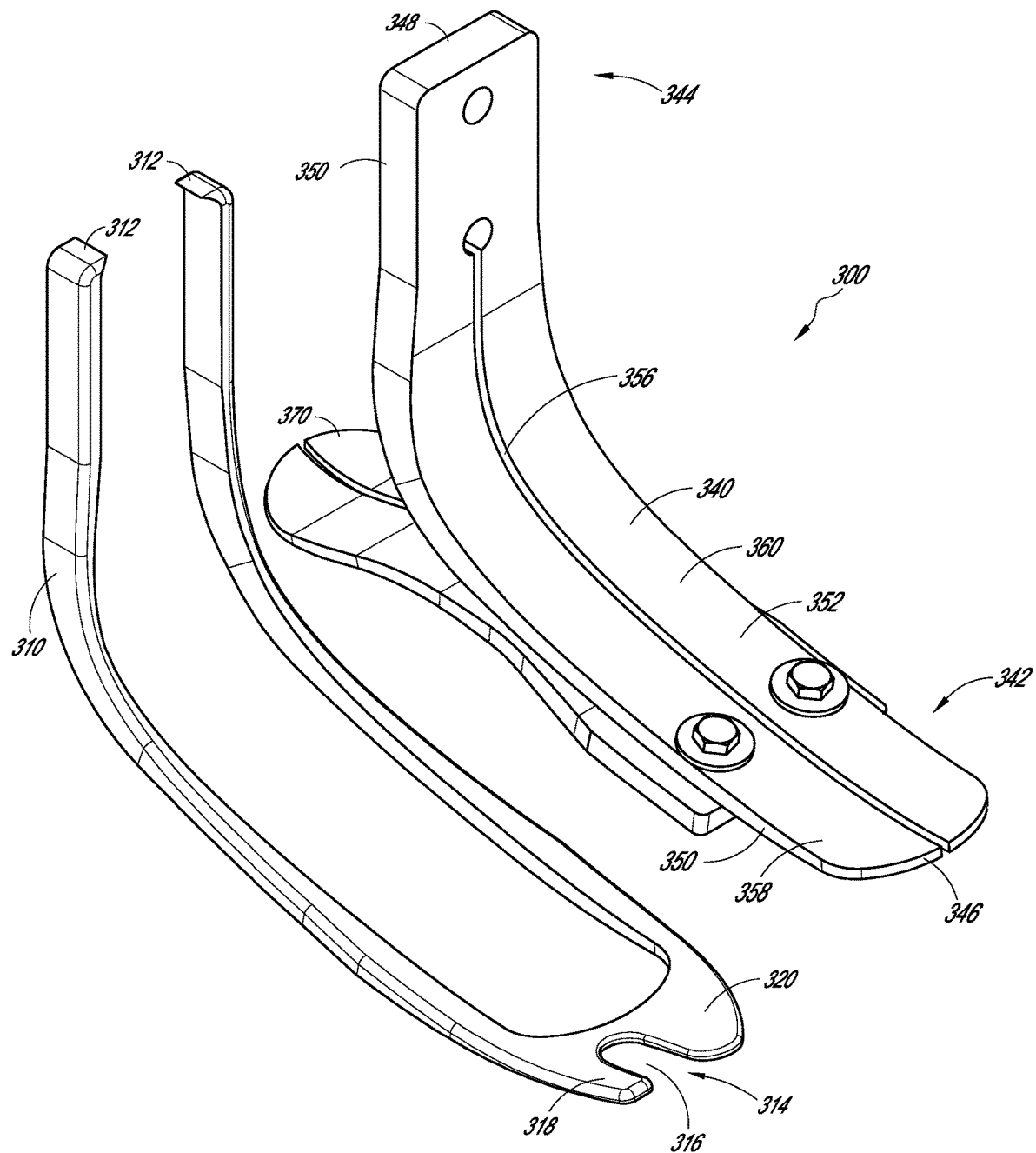
FIG. 11 is a partial side, top and front profile view of the prosthetic foot of FIG. 10 that can be coupled to an overmould attachment and an overmould attachment that can be coupled to a prosthetic foot, with the prosthetic foot and the overmould separated.
Figure 12:
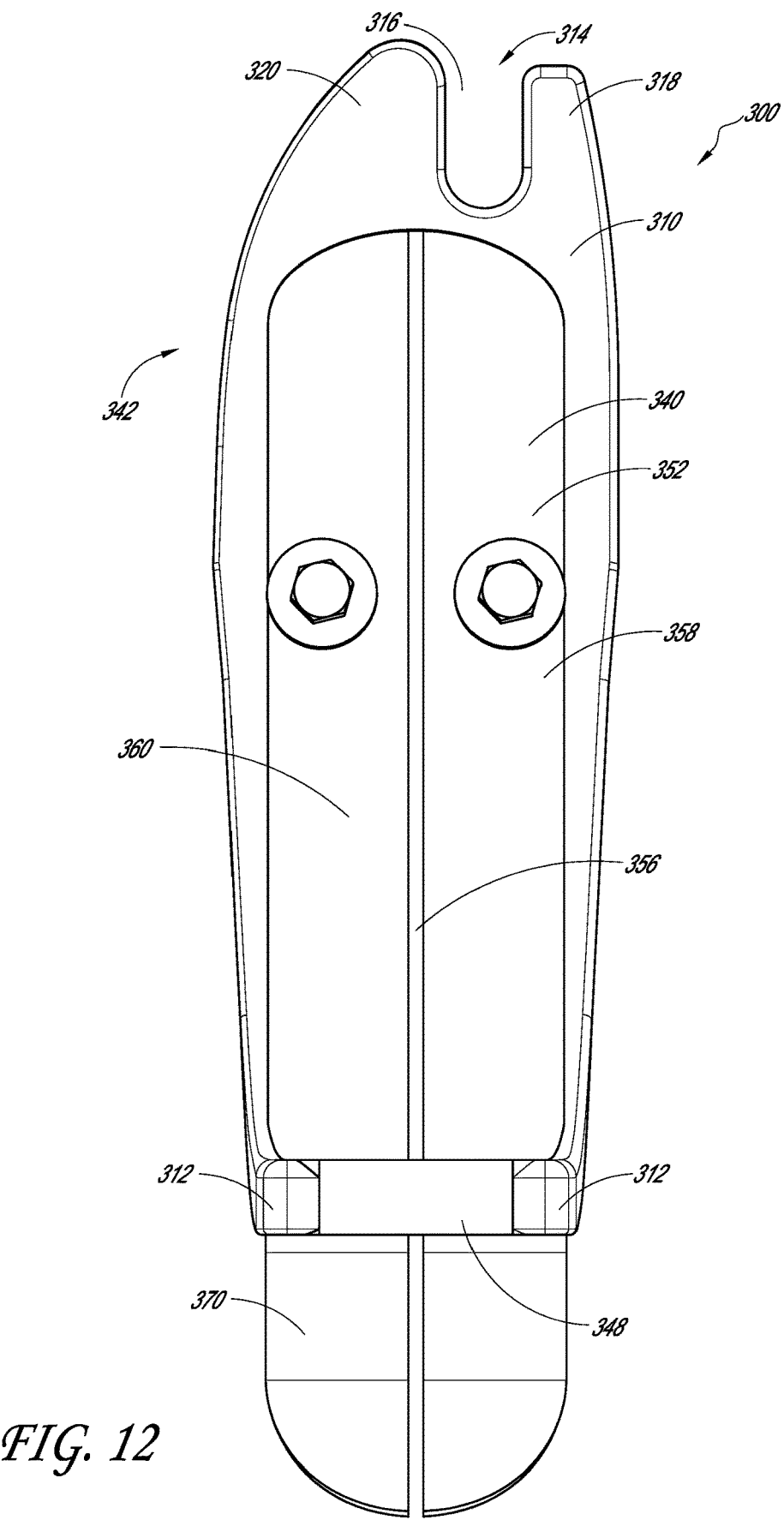
FIG. 12 is a top plan view of the overmould attachment coupled to the prosthetic foot of FIG. 10.

FIGS. 10-13 illustrate another embodiment of an overmould attachment 310 coupleable to a foot plate 340 of a prosthetic foot 300. The foot plate 340 generally can have a toe end 342 and an ankle end 344, as well as a toe surface 346, an ankle surface 348, and medial and lateral side surfaces 350 extending from the toe surface 346 to the ankle surface 348. In one embodiment, the medial and/or lateral side surfaces or edges 350 extend generally linearly between the toe end 342 and the ankle end 344 along at least a portion of their length. In another embodiment, the medial and or lateral side surfaces or edges 350 extend in a generally curved manner along at least a portion of their length between the toe end 342 and the ankle end 344. The foot plate 340 can have a top surface 352 and a bottom surface 354 opposite the top surface 352. Like the embodiments shown in FIGS. 1-5 and FIGS. 6-9, the embodiment of an overmould attachment 310 shown in FIGS. 10-13 is coupled or removably coupled to the toe surface 346 of foot plate 340 and along the side surfaces 350 of the foot plate 340 of a prosthetic foot 300. In one embodiment, the overmould attachment 310 is coupled or removably coupled along the entire side surfaces 350 of the foot plate 340. In some embodiments, as shown in FIGS. 10 and 12, at the ankle surface 346 of the foot plate 340, the overmould attachment 310 has portions 312 that extend at least partially over the ankle surface 348 of the foot plate 340. In some embodiments, the portions 312 of the overmould attachment 310 that extend at least partially over the ankle surface 348 help to couple the overmould attachment 310 to the foot plate 340. In some embodiments, the overmould attachment 310 extends at least partially over the top surface 352 of the foot plate 340 and at least partially over the bottom surface 354 of the foot plate 340. In some embodiments, the overmould attachment 310 extends at least partially over the top surface 352 of the foot plate 340. In some embodiments, the overmould attachment 310 extends at least partially over the bottom surface 354 of the foot plate 340. In some embodiments, the prosthetic foot 300 can have a heel plate 370, connected to the bottom surface 354 of the foot plate 340, extending away from the toe end 342. In one embodiment, the overmould attachment 10 is not coupled to the heel plate 370. In some embodiments, the overmould attachment 10 does not contact the heel plate 370.

In some embodiments, the foot plate 340 has a lengthwise split, 356 beginning at the toe end 342 of the foot plate and extending at least part of the length of the foot plate 340, that divides the foot plate 340, resulting in a medial portion 358 and a lateral portion 360. In some embodiments, the lengthwise split 356 does not span the entire length of the foot plate, resulting in an undivided foot plate at the ankle end 344 of the foot plate 340. In some embodiments, the attachment 310 can have a corresponding split (not shown)

at the toe end 342. The splits in the foot plate and the attachment can allow the medial and lateral portions 358 and 360 to flex at least somewhat independently, improving functional properties of the prosthetic foot during rollover and when used on uneven terrain.

Figure 13:
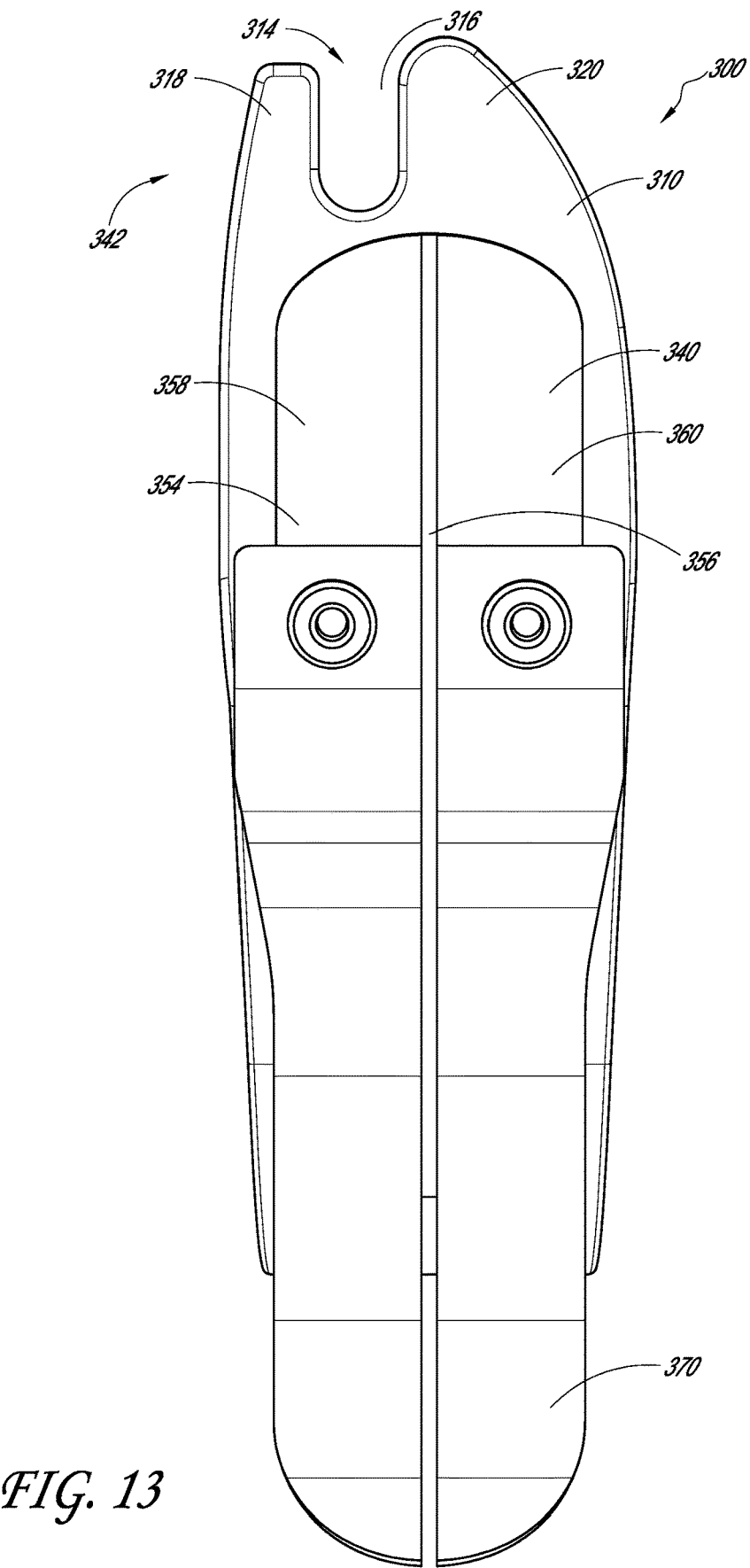
FIG. 13 is a bottom plan view of the overmould attachment coupled to the prosthetic foot of FIG. 10.
Figure 14:
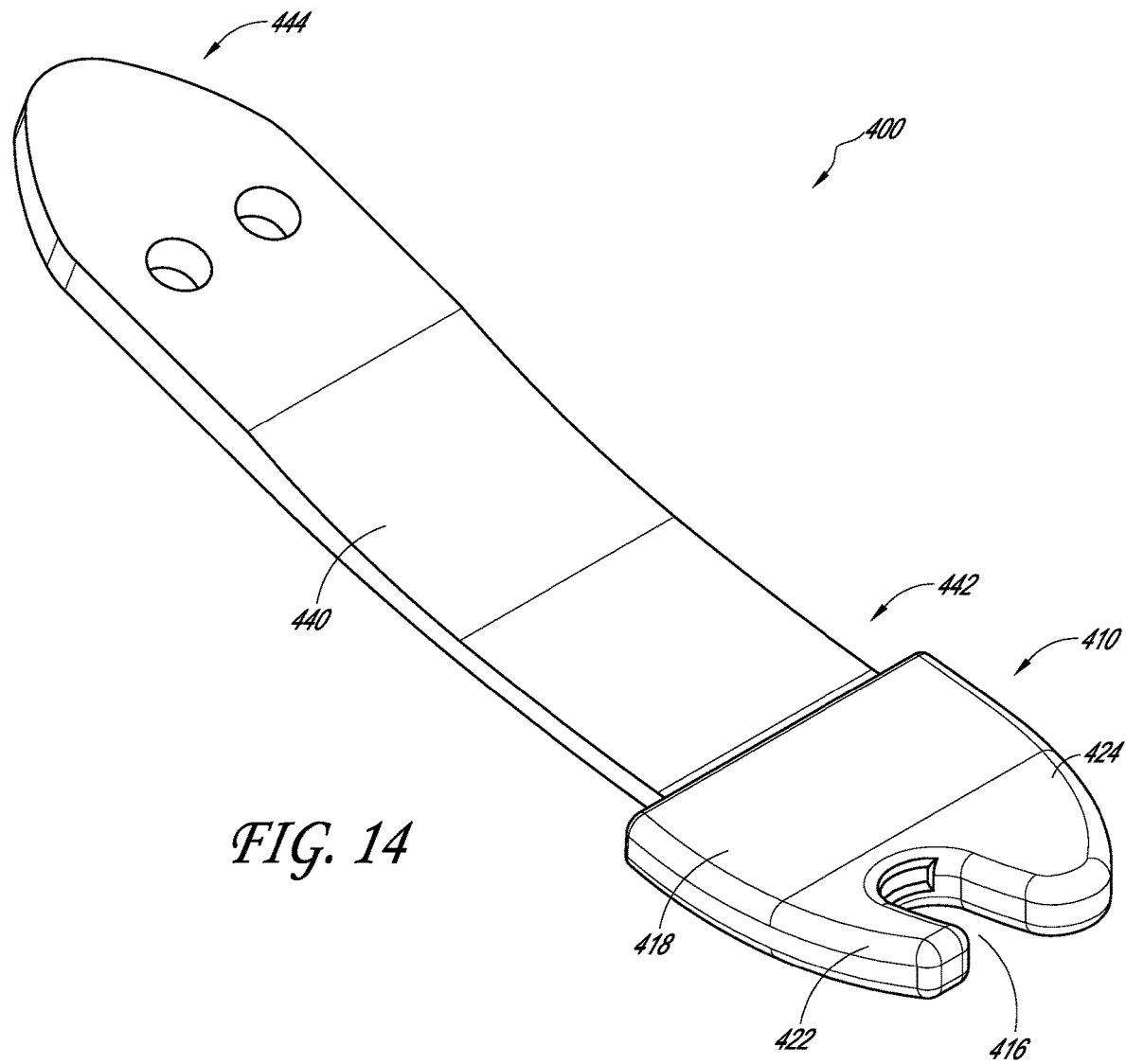
FIG. 14 is a partial side, top and front profile view of one embodiment of a toe attachment coupled to a prosthetic foot plate.
Figure 15:
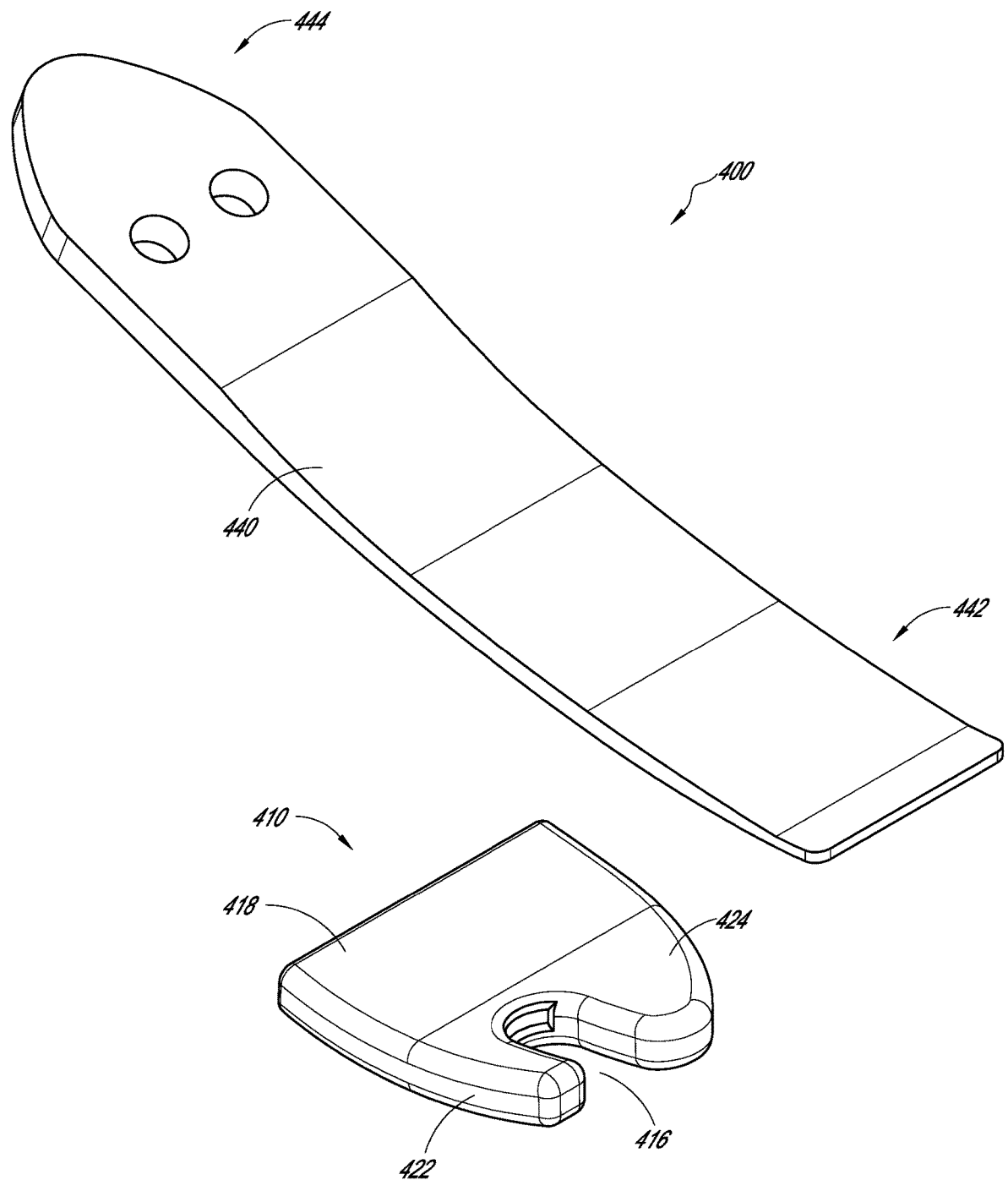
FIG. 15 is a partial side, top and front profile view of the prosthetic foot plate of FIG. 14 that can be coupled to a toe attachment and a toe attachment that can be coupled to a prosthetic foot plate, with the foot plate and the toe attachment separated.
Figure 16:
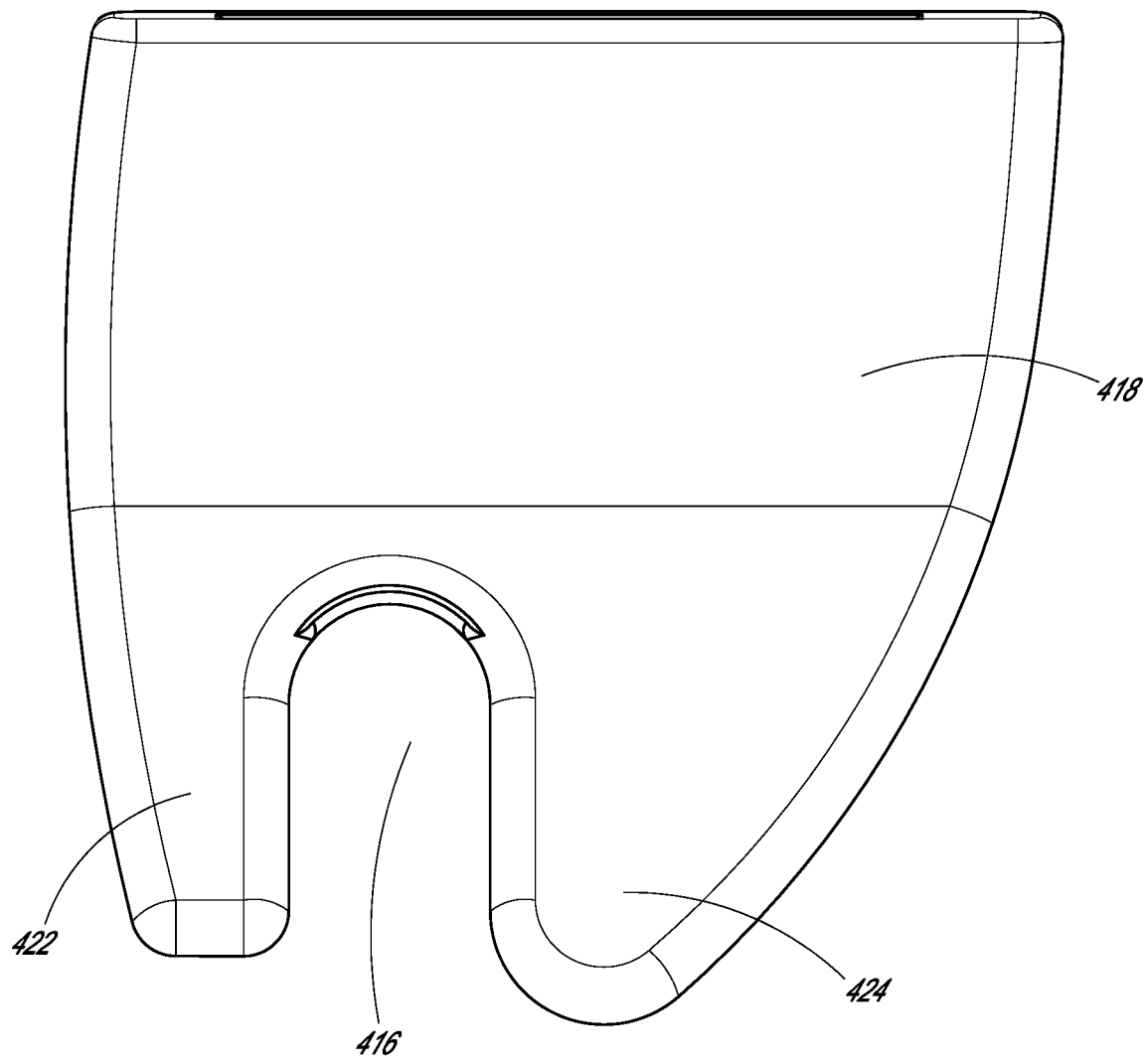
FIG. 16 is a top plan view of one embodiment of the toe attachment in FIG. 15.
Figure 17:
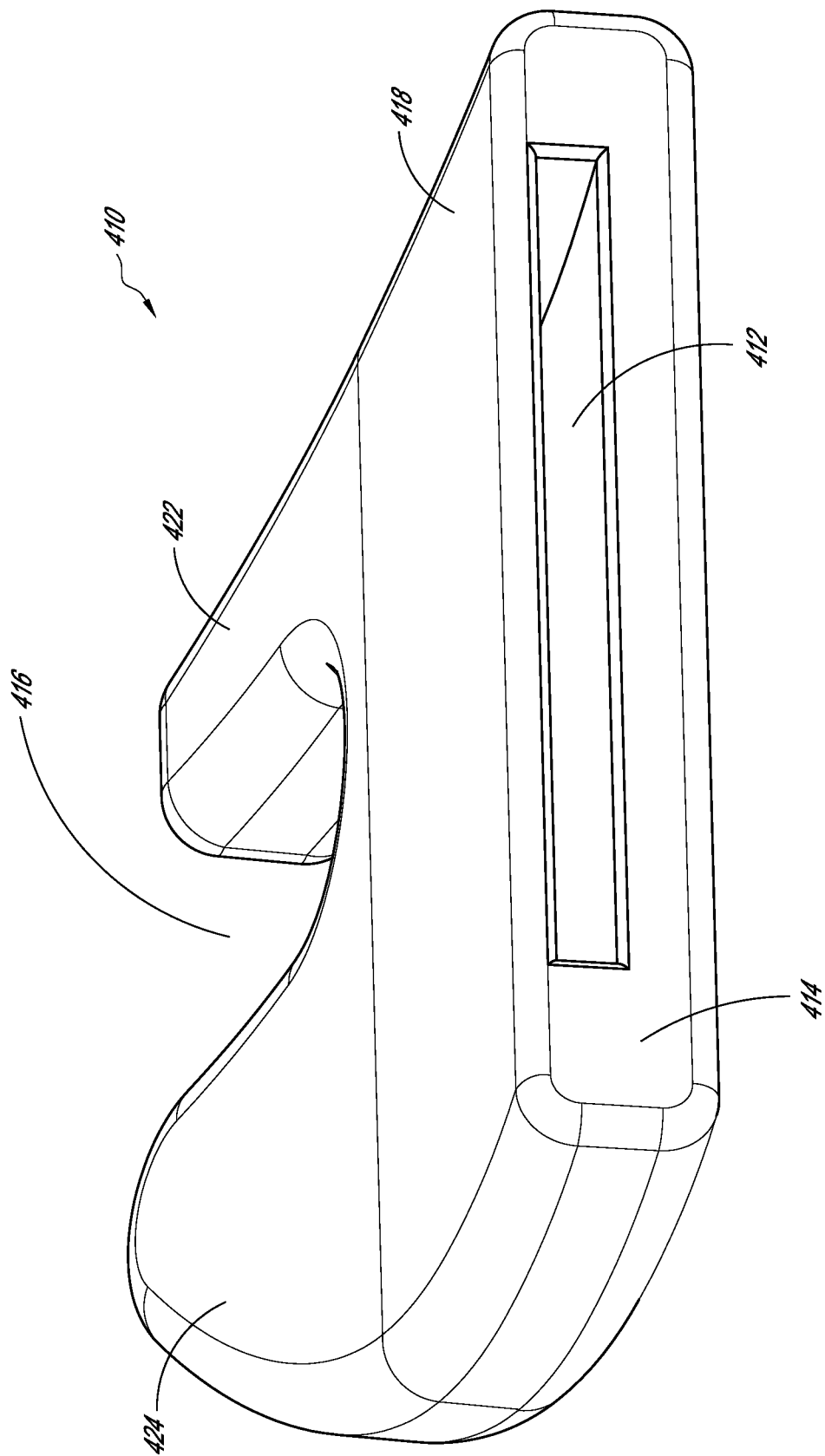
FIG. 17 is a partial rear, side, and top profile view of the toe attachment in FIG. 15, showing one embodiment of a cavity that can receive a prosthetic foot plate.
Figure 18:
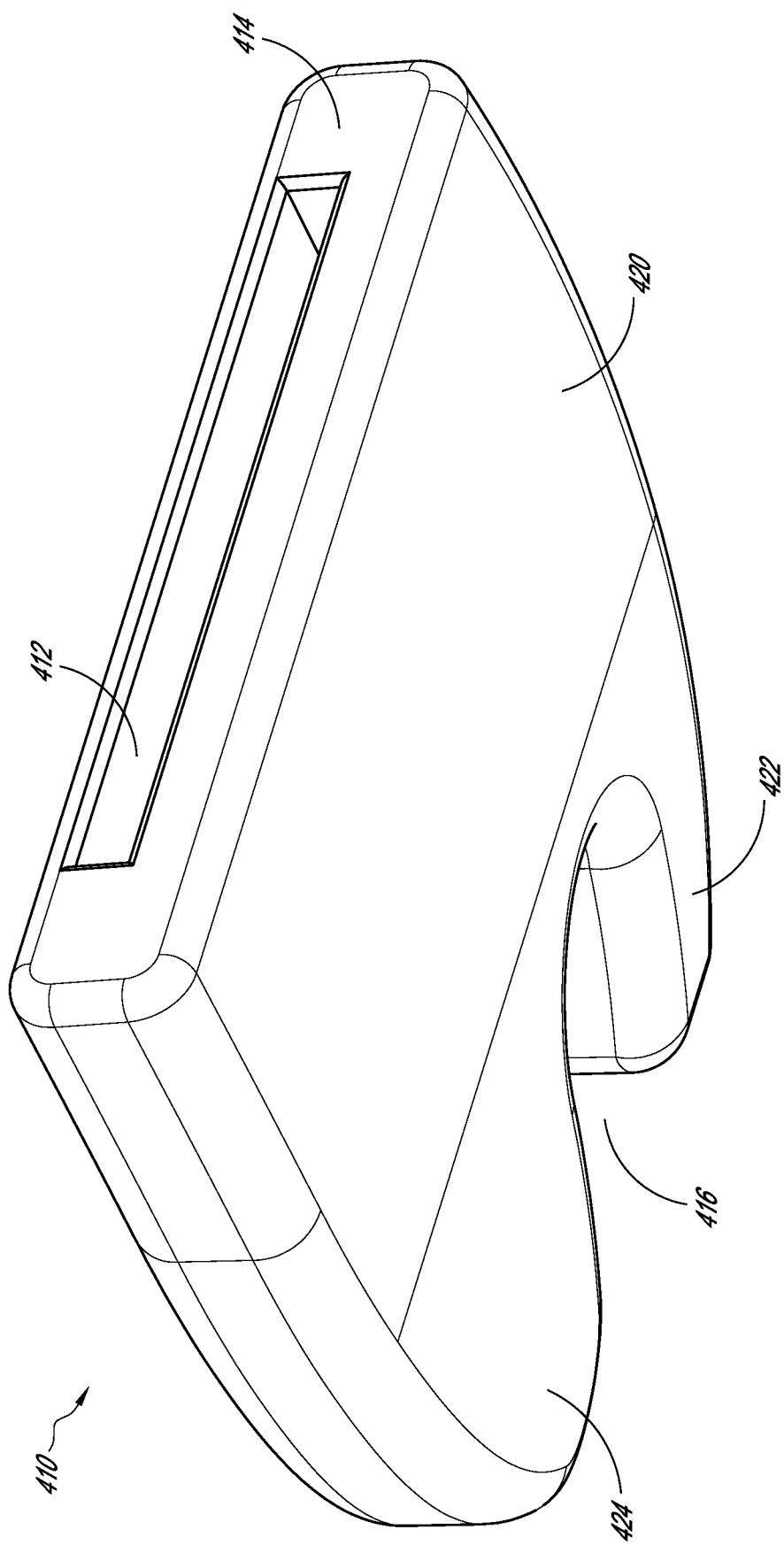
FIG. 18 is a partial rear, side, and bottom profile view of the toe attachment of FIG. 15, showing one embodiment of a cavity that can receive a prosthetic foot plate.
Figure 19:
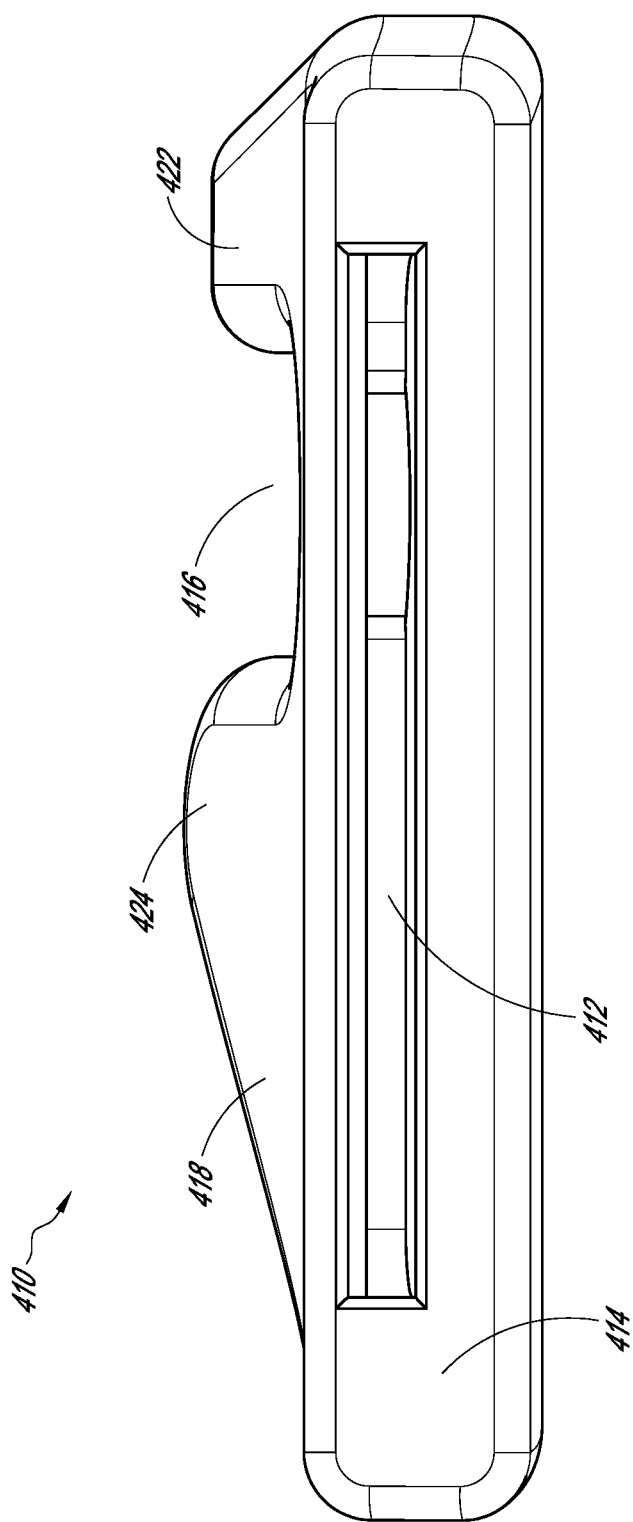
FIG. 19 is a rear profile view of the toe attachment of FIG. 15, showing one embodiment of a cavity that can receive a prosthetic foot plate.

In one embodiment, as seen in FIGS. 10, 12 and 13, the overmould attachment 310 is a single piece that advantageously changes the shape of the foot plate 340. In some embodiments, including the embodiment shown in FIGS. 10, 12 and 13, the overmould attachment 310 includes a portion 314 that extends the length of the toe of the foot plate 340, wherein the extended portion 314 includes a cutout section 316 that divides the extended portion 314 into a medial lobe 318 and a lateral lobe 320. In some embodiments, the cutout or slot 316 is generally U-shaped and sized to receive a strap of a sandal, flip-flop or similar footwear (e.g., the slot 316 provides a sandal toe feature). In some embodiments, both the medial lobe 318 and lateral lobe 320 can have a width. In some embodiments, the lateral lobe 320 has a width greater than the width of the medial lobe 318. In other embodiments, the medial lobe 318 has a width greater than the width of the lateral lobe 320. In still other embodiments, the medial lobe 318 and lateral lobe 320 have equal or approximately equal widths (e.g., the slot 316 can be located generally midway along the width of the foot 300). In some embodiments, the respective widths of the medial lobe 318 and lateral lobe 320 result in a stiffness for the medial lobe 318 and lateral lobe 320, wherein varying the widths of the medial lobe 318 and lateral lobe 320 results in varying the stiffness of the medial lobe 318 and lateral lobe 320. In some embodiments, the characteristics of the medial lobe 318 and lateral lobe 320 result in improved rollover during use of the prosthetic foot 300 coupled to the overmould attachment 310.

In some embodiments, this extended portion 314 including a cutout 316 allows the user to use the prosthetic foot 300 in combination with sandal-type shoes or other types of footwear without also having to use a cosmetic foot cover. In some embodiments, the overmould attachment 310 changes the width of the foot plate 340. In some embodiments, the overmould attachment 310 changes the length of the foot plate 340. In some embodiments, the overmould attachment 310 advantageously changes the shape of the foot plate 340 to make it more like the shape of a natural human foot (e.g., to include a sandal toe slot). In some embodiments, the overmould attachment 310 advantageously changes the shape of the foot plate 340 to improve stability characteristics of the prosthetic foot 300. In some embodiments, the overmould attachment 310 advantageously changes the shape of the foot plate 340 to improve functional characteristics of the prosthetic foot 300 during rollover.

In one embodiment, the overmould attachment 310 shown in FIGS. 10-13 can be removably coupled to a foot plate 340 of a prosthetic foot 300. In some embodiments, the overmould attachment 310 is coupled or removably coupled to the foot plate 340 using at least one clip mechanism. In some embodiments, the overmould attachment 310 is coupled or removably coupled to the foot plate 340 using a series of clips. In other embodiments, the overmould attachment 310 is coupled or removably coupled to the foot plate 340 using glue or epoxy. In other embodiments, the overmould attachment 310 is coupled or removably coupled to the foot plate 340 using magnetic force. In other embodiments, the overmould attachment 310 is coupled to the foot plate 340 using a series of complementary magnets located at corresponding locations of the overmould attachment 310 and foot plate 340. In still other embodiments, the overmould attachment 310 is coupled to the foot plate 340 using elastic properties of at least one part of the overmould attachment 310. In some embodiments, the overmould attachment 310 is coupled to the foot plate 340 using any method of coupling known in the art. In some embodiments, the overmould attachment 310 is coupled to the foot plate 340 using any combination of any of the aforementioned coupling mechanisms.

In some embodiments, the overmould attachment 310 is made of a polymer or plastic-like material or a compressible material. In some embodiments, the overmould attachment 310 is the same stiffness as the foot plate 340. In some embodiments, the overmould attachment 310 is cheaper and easier to manufacture than the foot plate 340. In some embodiments, the overmould attachment 310 protects the foot plate 340 of the prosthetic foot 300 from damage due to everyday wear and tear.

FIGS. 14-20 illustrate one embodiment of a toe attachment 410 coupleable to a foot plate 440 of a prosthetic foot 400. The foot plate 440 can be generally planar (e.g., generally flat) and have a toe end 442 and an ankle end 444, as well as a toe surface 446, an ankle surface 448, and medial and lateral side surfaces 450 extending from the toe surface 446 to the ankle surface 448. In the embodiment shown in FIG. 14, the toe attachment 410 is coupled to the toe end 442 of a foot plate 440 for a prosthetic foot 400. In some embodiments, the toe attachment 410 is removably coupleable to the foot plate 440. In some embodiments, the toe attachment 410 can have a cavity 412 on a rear surface 414, shown in FIGS. 17-19, wherein the cavity can receive the toe end 442 of a foot plate 440 such that the toe attachment 410 is coupled or removably coupled to the toe end 442 of the foot plate 440. In some embodiments, the toe attachment 410 is coupled or removably coupled to a foot plate 440 using at least one clip. In some embodiments, the toe attachment 410 is coupled or removably coupled to a foot plate 440 using glue or epoxy. In still another embodiment, the toe attachment 410 is coupled or removably coupled to a foot plate 440 using magnetic force. In some embodiments, the toe attachment 410 is coupled to the foot plate 440 using any method of coupling known in the art. In some embodiments, the toe attachment 410 is coupled to the foot plate 440 using any combination of any of the aforementioned coupling mechanisms.

Figure 20:
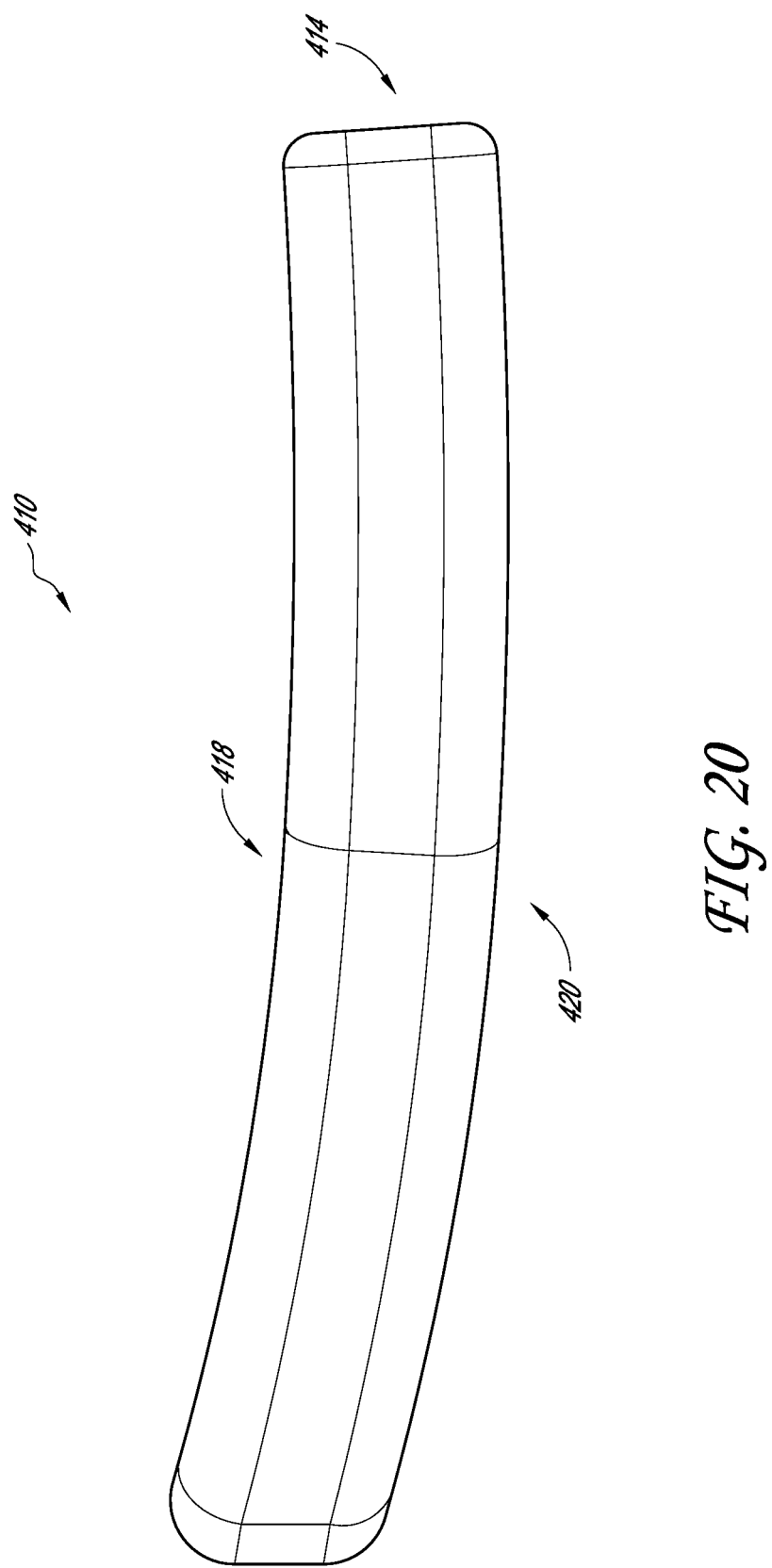
FIG. 20 is a side profile view of the toe attachment of FIG. 15.
Figure 21:
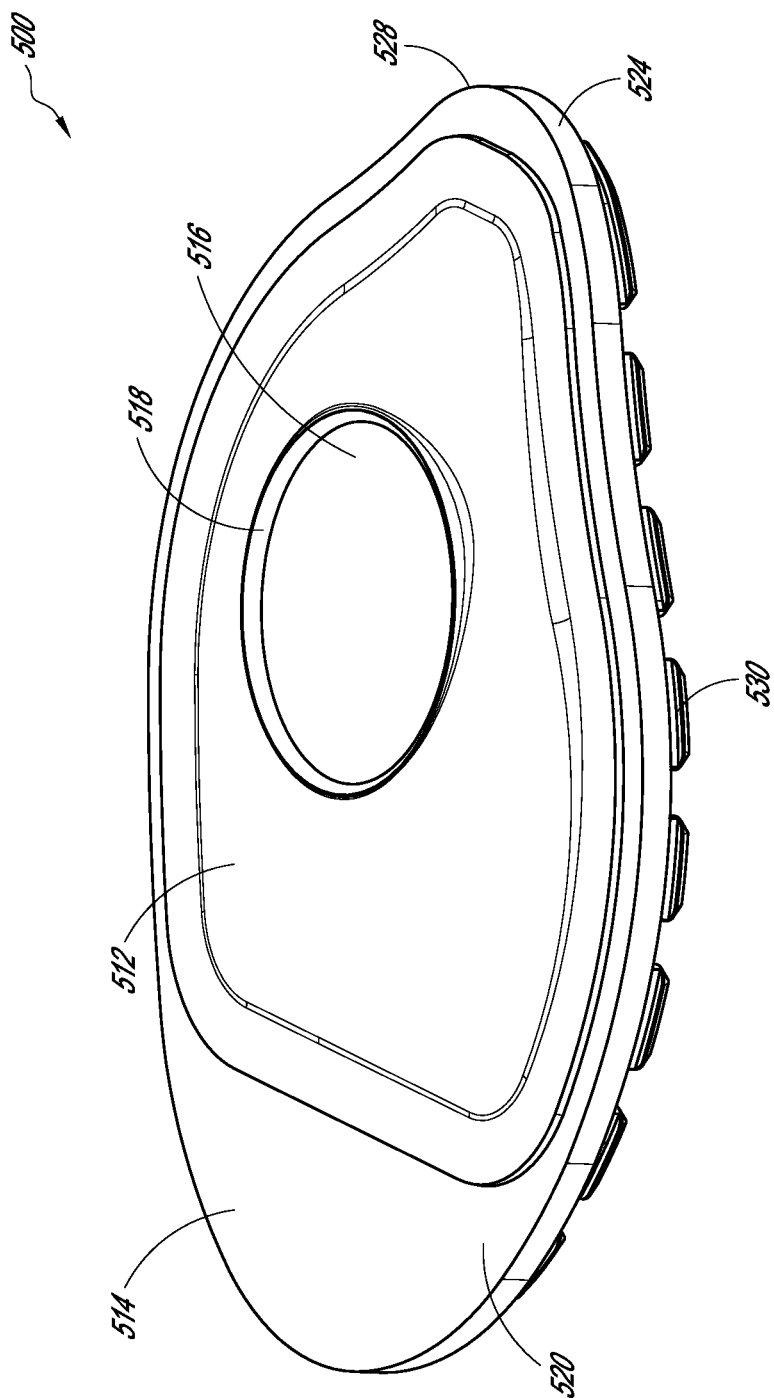
FIG. 21 is a partial side, top and front profile view of one embodiment of a seal cover for a prosthetic foot.
Figure 22:
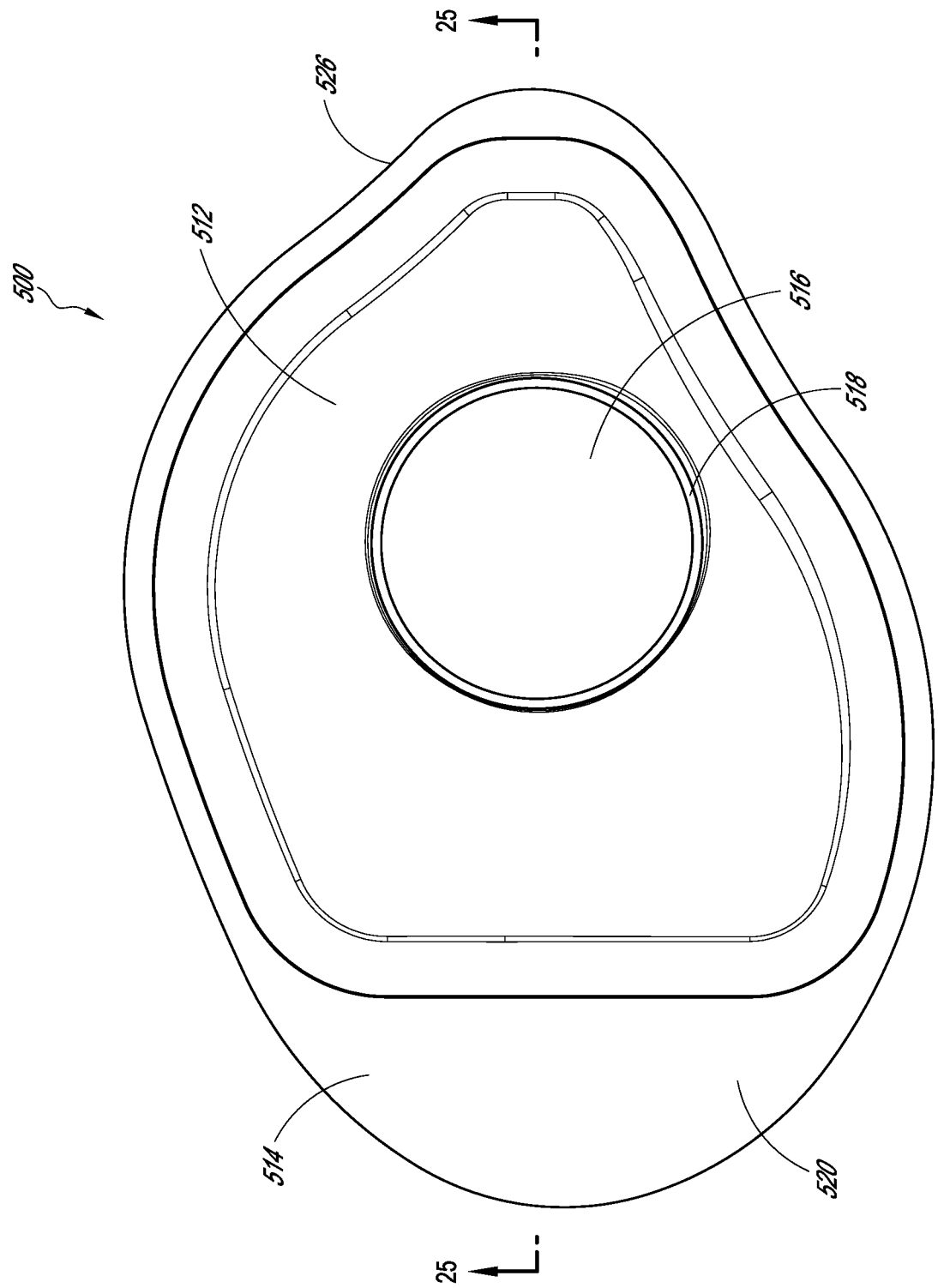
FIG. 22 is a top plan view of the seal cover of FIG. 21.
Figure 23:
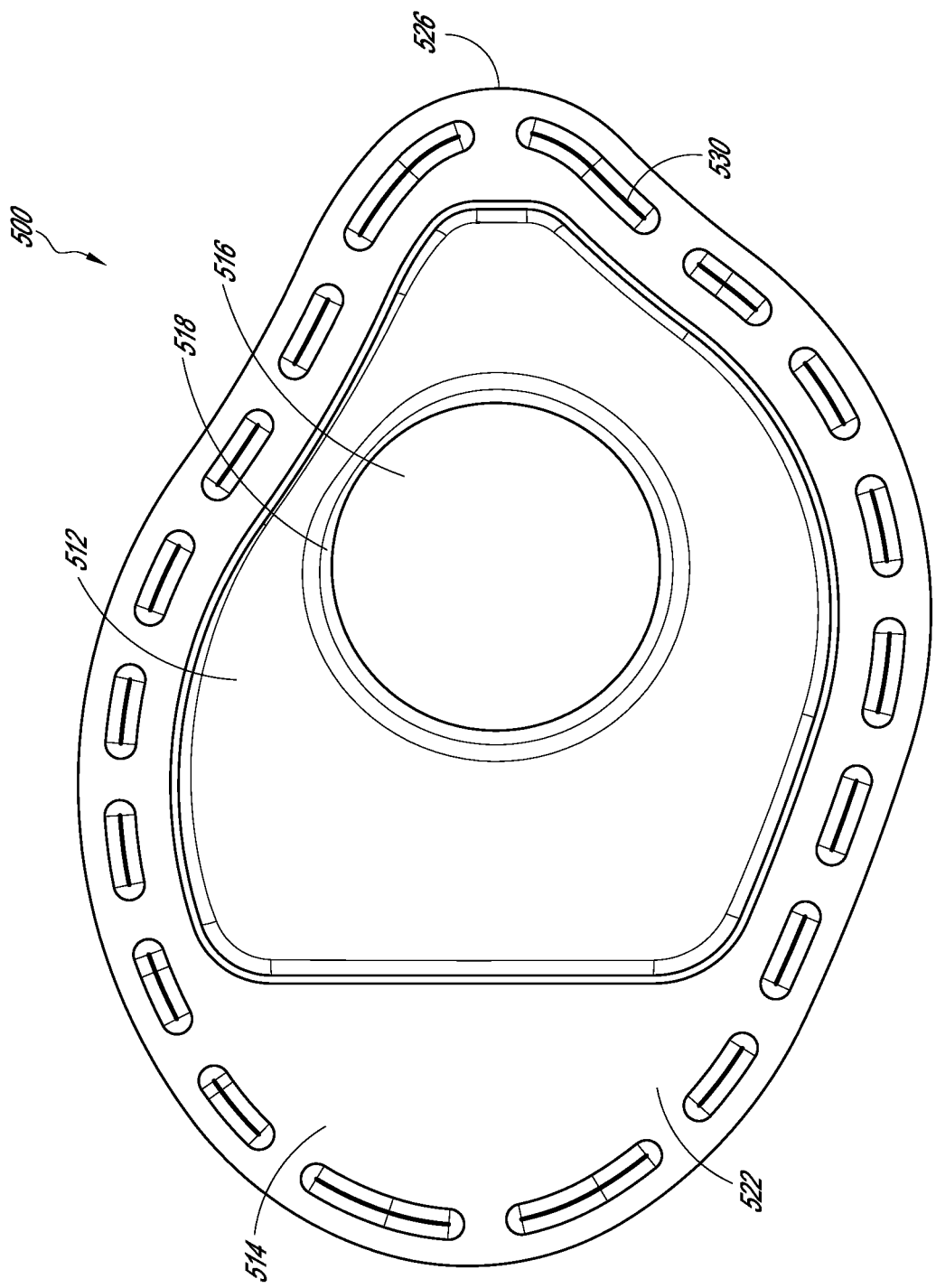
FIG. 23 is a bottom plan view of the seal cover of FIG. 21.
Figure 24:
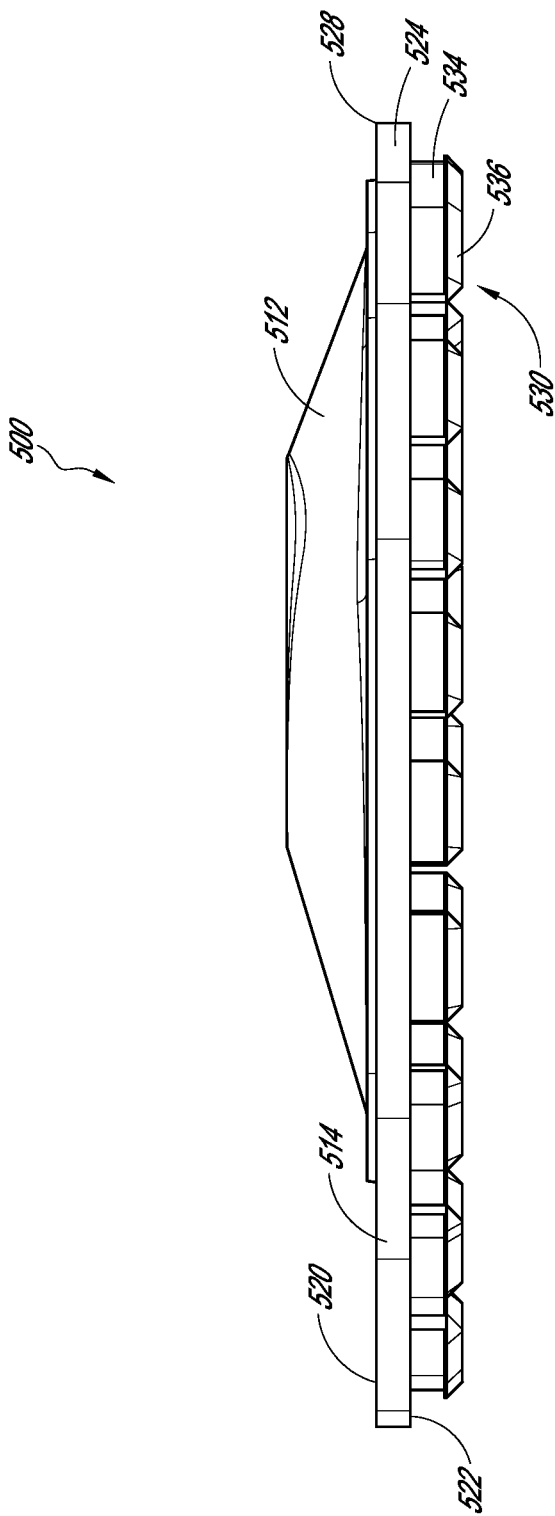
FIG. 24 is a side profile view of the seal cover of FIG. 21.

In some embodiments, the toe attachment 410 can have a top surface 418 and a bottom surface 420. In some embodiments, the top surface 418 and the bottom surface 420 are substantially parallel. In some embodiments, as shown in FIG. 20, the top surface 418 and the bottom surface 420 have a slight upward curve as they move away from rear surface 414. In some embodiments, the toe attachment 410 can have a cutout or slot 416 that extends from the top surface 418 to the bottom surface 420 that divides the toe attachment 410 into a medial lobe 422 and a lateral lobe 424. In some embodiments, the cutout or slot 416 is generally U-shaped and sized to receive a strap of a sandal, flip-flop or similar footwear (e.g., the slot 416 can provide a sandal toe feature). In some embodiments, the cutout 416 resulting in a medial lobe 422 and lateral lobe 424 gives the toe attachment 410 a more anatomical appearance. In some embodiments, the more anatomical appearance is a "sandal toe" appearance. In some embodiments, both the medial lobe 422 and lateral lobe 424 can have a width. In some embodiments, the medial lobe 422 has a width greater than the width of the lateral lobe 424. In other embodiments, the lateral lobe 424 has a width greater than the width of the medial lobe 422. In still other embodiments, the medial lobe 422 and lateral lobe 424 have equal or approximately equal widths (e.g., the slot 416 can be located generally midway along the width of the foot 400). In some embodiments, the respective widths of the medial lobe 422 and lateral lobe 424 result in a stiffness for the medial lobe 422 and lateral lobe 424, wherein varying the widths of the medial lobe 422 and lateral lobe 424 results in varying the stiffness of the medial lobe 422 and lateral lobe 424. In some embodiments, this stiffness of the medial lobe 422 and lateral lobe 424 improve the functional characteristics of the prosthetic foot 400 during rollover. Additionally, when coupled to a foot plate 440, the toe attachment 410 facilitates use of the prosthetic foot 400 with sandal-type shoes or other footwear without the use a cosmesis.

FIGS. 21-25 illustrate one embodiment of a seal cover 500 for a cosmetic cover (e.g., cosmesis) for a prosthetic foot. In some embodiments, the seal cover 500 generally has the shape of the cross-section of a human ankle. In some embodiments, the seal cover 500 generally has the shape of the ankle opening of a cosmetic cover for a prosthetic foot. The seal cover 500 generally can have an inner portion 512 and an outer portion 514. In some embodiments, the inner portion 512 and the outer portion 514 are made of different materials. In some embodiments, the inner portion 512 is a membrane made of a flexible material. In some embodiments, the flexible material is elastic. In some embodiments, the outer portion 514 is a frame made of plastic (e.g., a hard plastic). However, other suitable materials can be used. In still another embodiment, the inner portion 512 and the outer portion 514 can be made of the same material.

The inner portion 512 can have a circular opening 516 that can fit over (e.g., engage) a portion of a prosthetic foot 542 or prosthetic component (e.g., pylon) 544 or 546, resulting in a substantially watertight connection 560 between the inner portion 512 and the prosthetic foot 542 or prosthetic foot component 544 or 546. In some embodiments, the circular opening 516 can have an O-ring 518. In some embodiments, the opening 516 of the inner portion 512 fits over (e.g., engages) an adaptor of a prosthetic foot. In some embodiments, the opening 516 of the inner portion 512 fits around (e.g., engages) a shank of a prosthetic foot. In some embodiments, the opening 516 of the inner portion 512 engages a collar adaptor located on a prosthetic foot (e.g., the collar adaptor 700 shown in FIG. 31 and described below), the collar adaptor having a groove that can receive the O-ring 518 of the opening 516. In some embodiments, when the opening 516 is engaged with the corresponding portion of a prosthetic foot 544, the connection 560 between the inner portion 512 and the prosthetic foot is substantially watertight.

In some embodiments, the outer portion 514 can have a top surface 520, a bottom surface 522, and an edge 524 defining a perimeter 526. The edge 524 and the top surface 520 form a corner 528 around the perimeter 526 of the outer portion 514, and, in some embodiments, this corner 528 is rounded off. In some embodiments, the top surface 520 is substantially flat. In some embodiments, the perimeter 526 has generally the shape of the ankle opening of a cosmetic cover 540 for a prosthetic foot 542. The outer portion 514 can engage a cosmetic cover 540 for a prosthetic foot 542. In some embodiments, the outer portion 514 can removably engage a cosmetic cover 540 for a prosthetic foot 542. In some embodiments, the bottom surface 522 can engage a cosmetic cover 540 for a prosthetic foot 542. In some embodiments, the bottom surface 522 has a series of protrusions 530 that can removably engage complementary cavities on the cosmetic cover 540. In some embodiments, the bottom surface 522 can engage a cosmetic cover 540 such that the connection 550 between the outer portion 514 and the cosmetic cover is substantially watertight. In some embodiments, glue or epoxy can be used at the connection 550 between the outer portion 514 and the cosmetic cover to improve the seal of the connection 550.

In some embodiments, the series of protrusions 530 is generally located around the perimeter 526 of the outer portion 514. In some embodiments, the series of protrusions 530 generally located around the perimeter 526 of the outer portion 514 are offset in from the edge 524 of the outer portion 514 such that when the outer portion 514 is engaged with a cosmetic cover, the edge 524 of the outer portion 514 is substantially flush with an outer surface of the cosmetic cover 540. In some embodiments, the protrusions 530 mate with corresponding recess openings or slots on a surface of the opening of the cosmetic cover 540. In some embodiments, the protrusions 530 are equally spaced around the perimeter 526 of the outer portion 514. In some embodiments, the spacing between the protrusions 530 can vary. In some embodiments, the series of protrusions 530 can have any number of protrusions. In some embodiments, the number of protrusions 530 is between 1 and 30. In some embodiments, there are about 15-20 protrusions in the series of protrusions 530. In some embodiments, there are 18 protrusions in the series of protrusions 530.

In some embodiments, a protrusion 530 can have a height, a length, a width, and a first and second cross-sectional faces 532, the cross-sectional faces 532 having a shape comprising a body 534 having a rectangular cross-section and a head 536 having an inverted triangular cross-section. The head 536 is located on the portion of the protrusion 530 farthest away from the bottom surface 522. In some embodiments, the triangular portion of the first and second cross-sectional faces 532 is angled inwards towards the opposite cross-sectional face. In some embodiments, the triangular head 536 has a width greater than the width of the rectangular body 534 such that the width of the triangle extends beyond the width of the rectangle. The height of a protrusion 530 is defined by the distance from the bottom surface 522 to the tip of the head 534 of the protrusion 530. In some embodiments, all protrusions 530 have equal heights. In some embodiments, the protrusions 530 have varying heights. In some embodiments, the height of a single protrusion 530 can be between about 0.1 cm to about 10 cm. In some embodiments, the height of a single protrusion 530 can be between about 0.1 cm to about 3 cm. The length of a protrusion 530 is defined by the distance from the first cross-sectional face to the second cross-sectional face. The length of a single protrusion 530 can vary between about 0.1 cm to about 10 cm. In some embodiments, the length of a single protrusion 530 can be between about 0.1 cm to about 3 cm. In some embodiments, all protrusions 530 have generally equal lengths. In some embodiments, protrusions 530 can have varying lengths. In some embodiments, the protrusions 530 are generally straight between the first and second cross-sectional faces 532. In some embodiments, the protrusions 530 curve between the first and second cross-sectional faces 532. In some embodiments, the protrusions 530 curve between the first and second cross-sectional faces 532 such that they run generally parallel to the perimeter 526 of the outer portion 514.

Figure 25A:
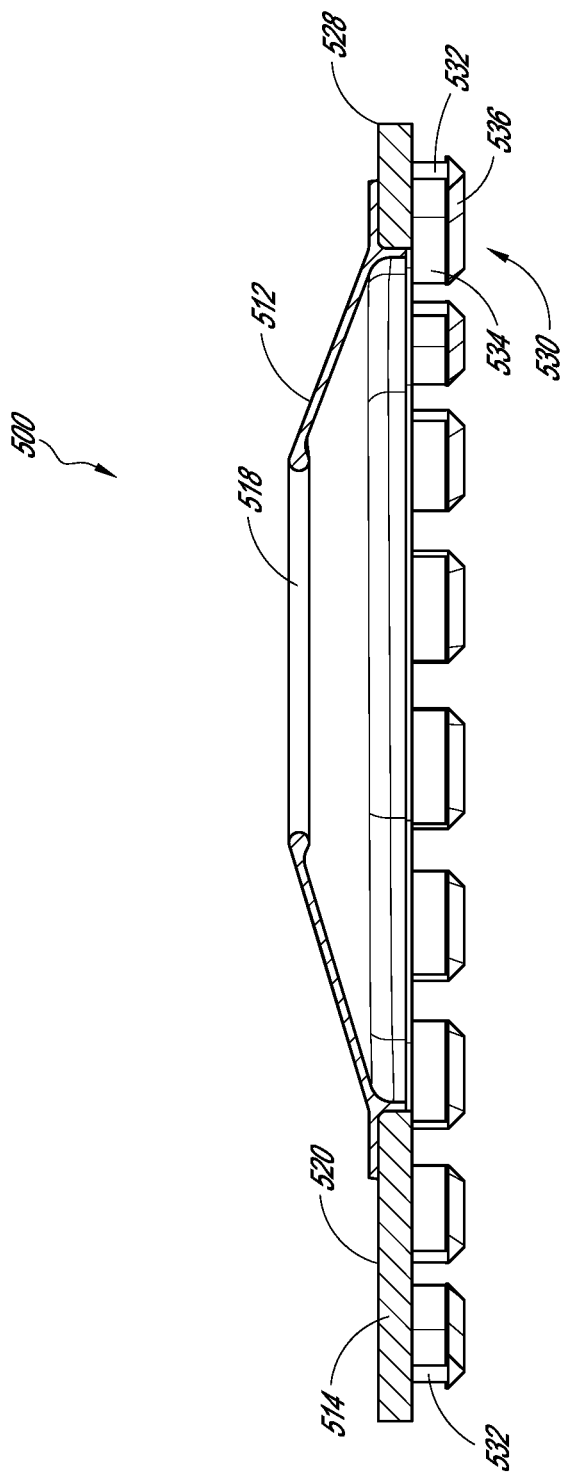
FIG. 25A is a cross-sectional view of the seal cover of FIG. 21, as viewed along plane 25-25 in FIG. 22.
Figure 25B:
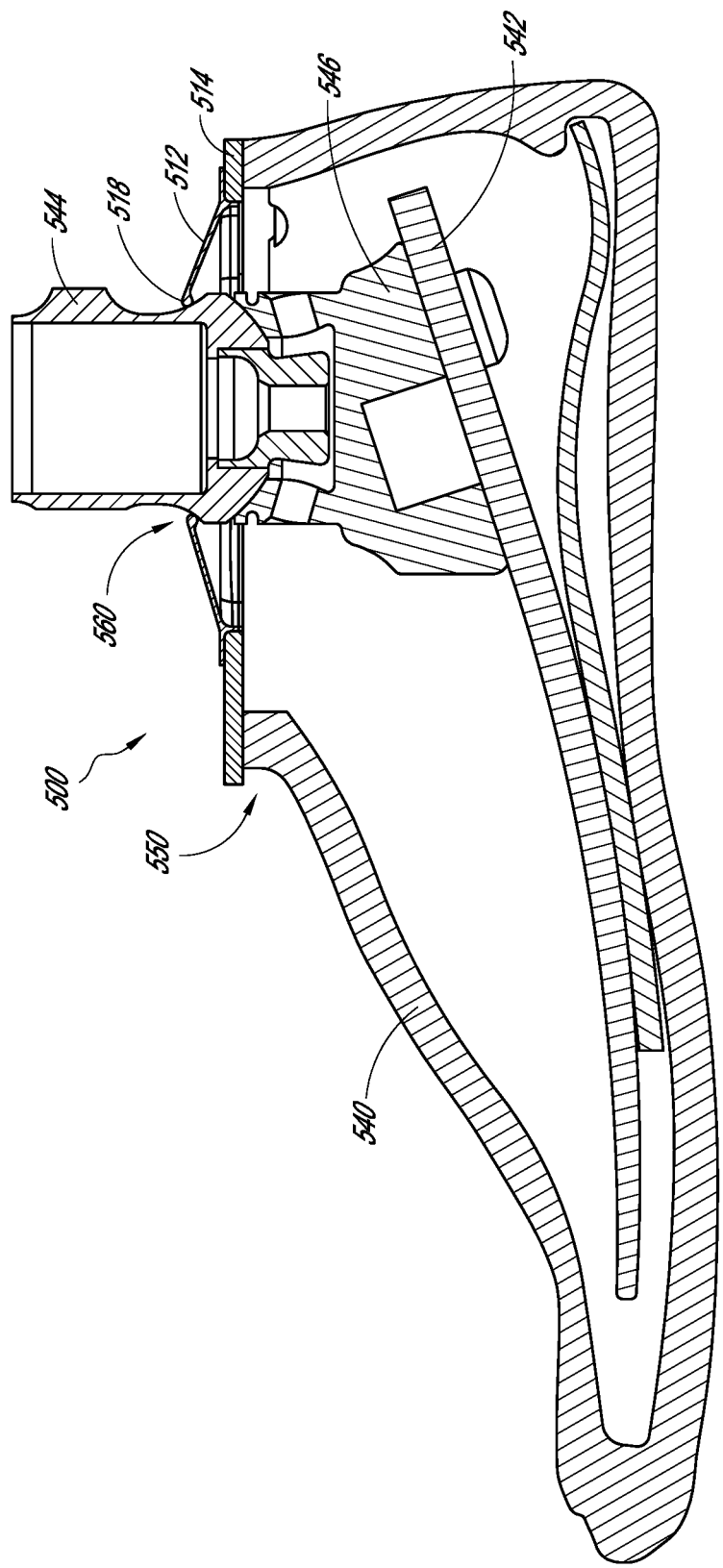
FIG. 25B is a cross-sectional view of one embodiment of the seal cover of FIG. 21 engaged with a cosmetic cover and a prosthetic foot system.
Figure 26:
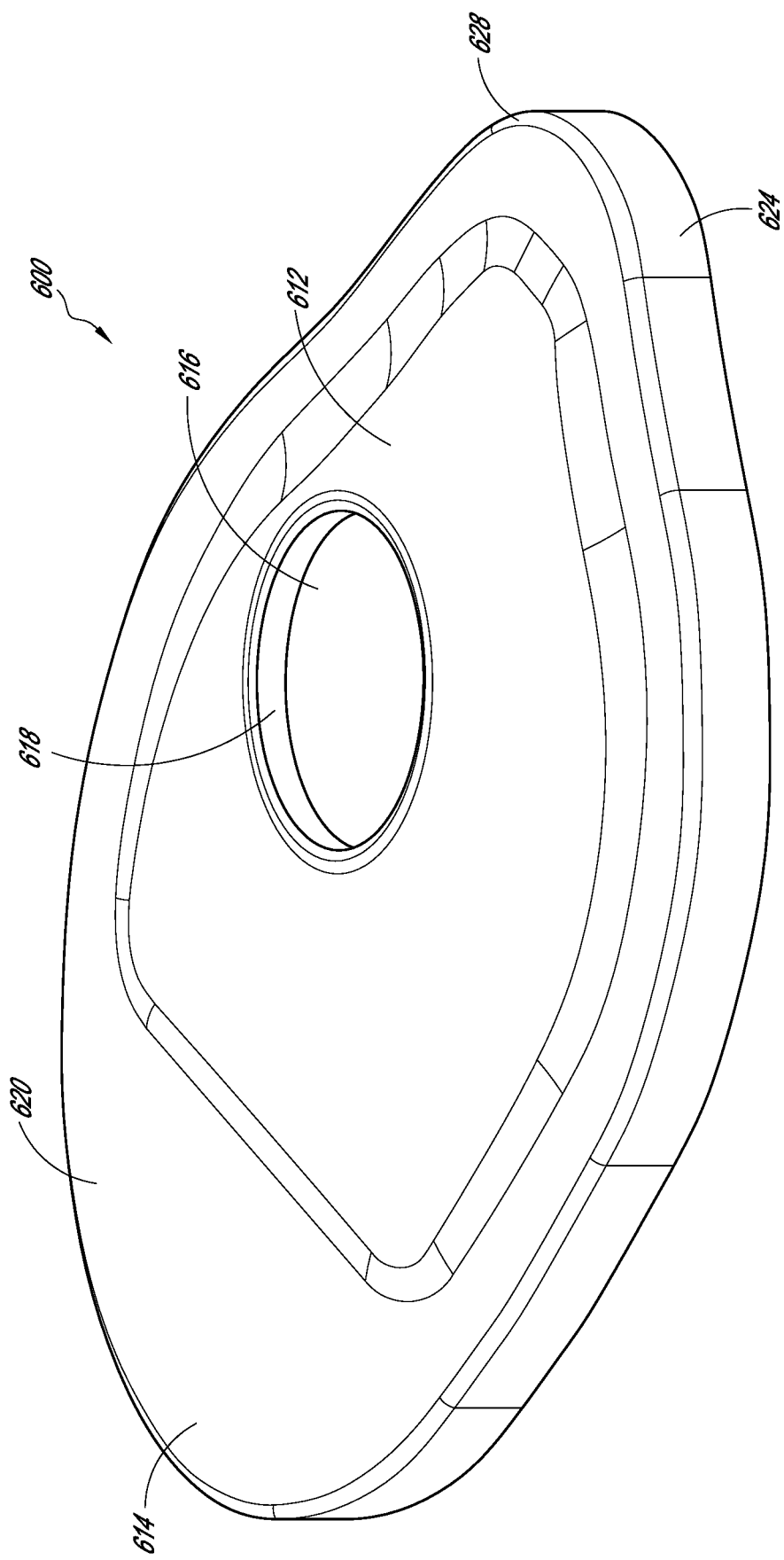
FIG. 26 is a partial side, top and front profile view of another embodiment of a seal cover for a prosthetic foot.
Figure 27:
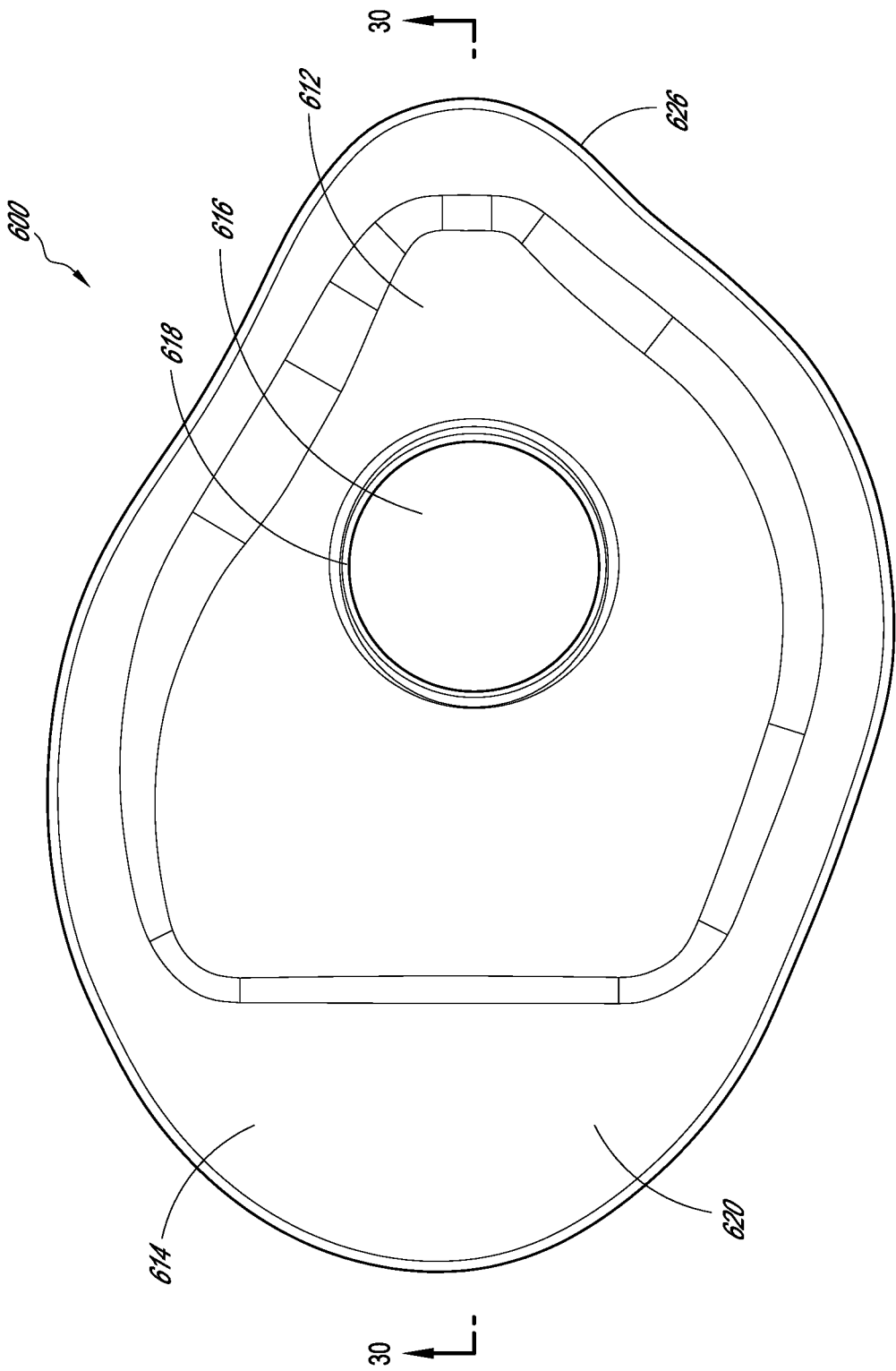
FIG. 27 is a top plan view of the seal cover of FIG. 26.
Figure 28:
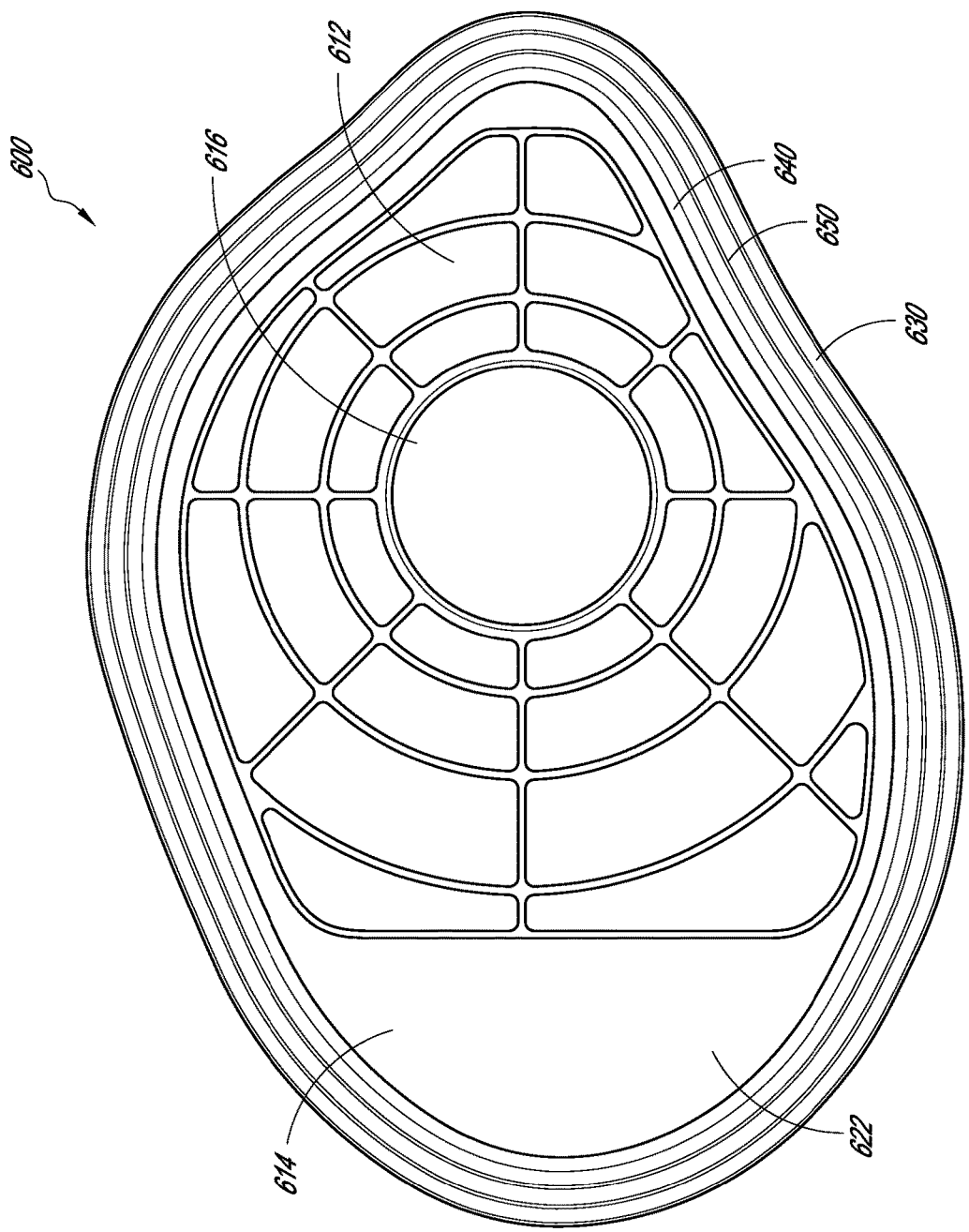
FIG. 28 is a bottom plan view of the seal cover of FIG. 26.
Figure 29:
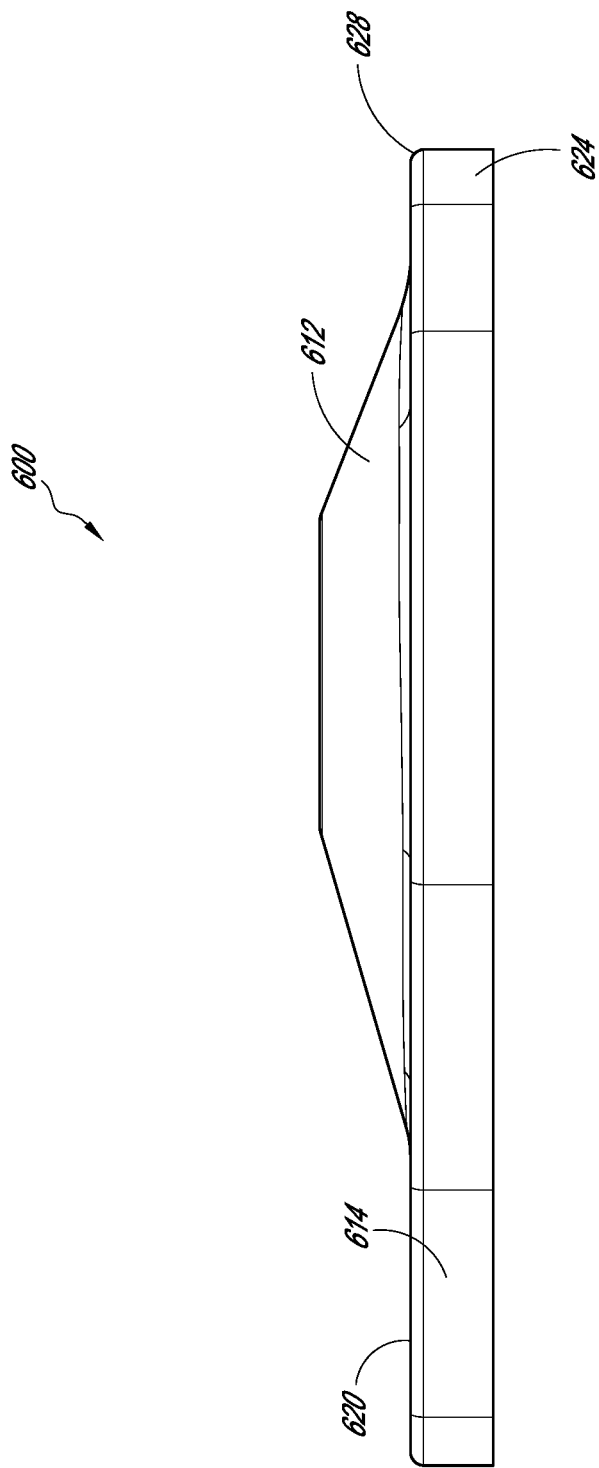
FIG. 29 is a side profile view of the seal cover of FIG. 26.
Figure 30:
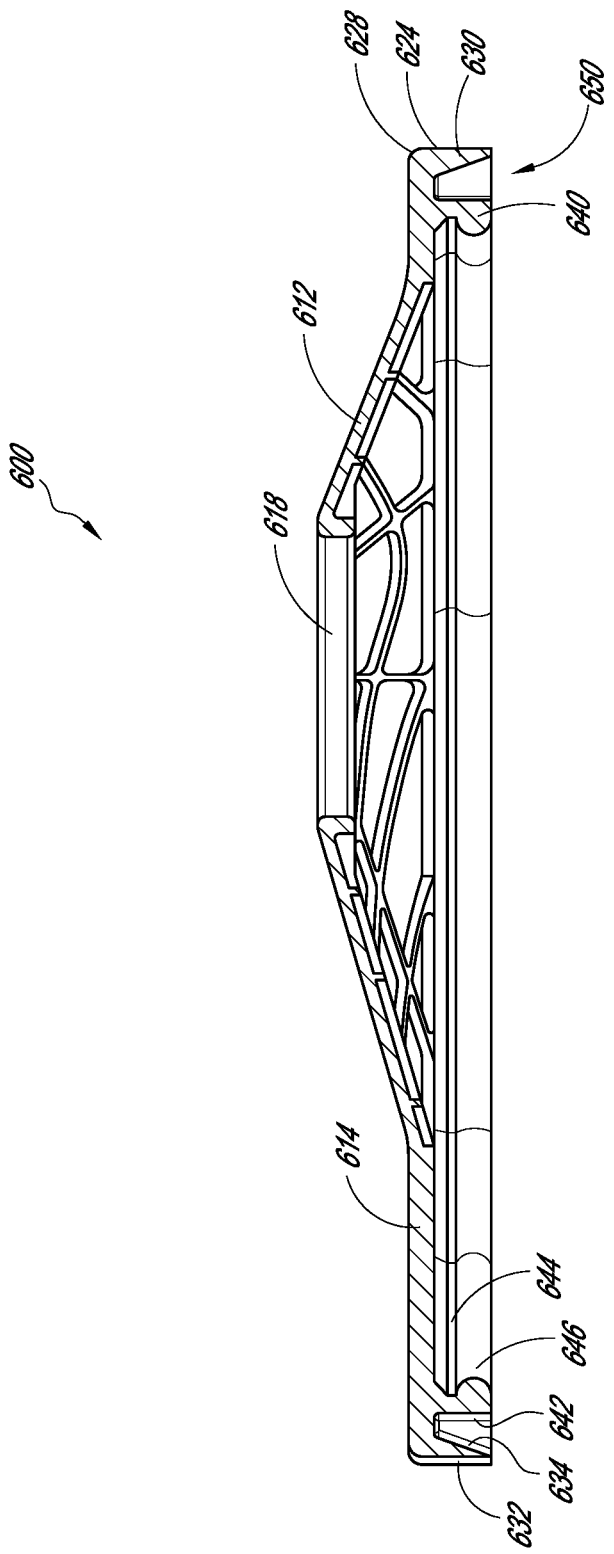
FIG. 30 is a cross-sectional view the seal cover of FIG. 26, as viewed along plane 30-30 in FIG. 27.

FIG. 25B illustrates one embodiment of a seal cover 500 engaged with a cosmetic cover 540 and fitted around (e.g., engaged with) a prosthetic foot system. In some embodiments, the outer portion 514 of the seal cover 500 is engaged with the cosmetic cover 540 such that the connection 550 between the outer portion 514 and the cosmetic cover 540 is substantially watertight. In some embodiments, the inner portion 512 of the seal cover 500 fits around (e.g., engages) a component 542, 544 or 546 of a prosthetic foot system such that the connection 560 between the inner portion 512 and the prosthetic foot system is substantially watertight. In some embodiments, the inner portion 512 of the seal cover 500 fits around (e.g., engages) a collar adaptor (e.g., the collar adaptor 700 shown in FIG. 31 and described below) located on or around a component of a prosthetic foot system, wherein the collar adaptor can have a groove to receive the inner portion 512. In some embodiments, the inner portion 512 can have varying shapes or designs.

FIGS. 26-30 illustrate one embodiment of a seal cover 600 for a cosmetic cover for a prosthetic foot. In some embodiments, the seal cover 600 generally has the shape of the cross-section of a human ankle. In some embodiments, the seal cover 600 generally has the shape of the ankle opening of a cosmetic cover for a prosthetic foot. The seal cover 600 generally can have an inner portion 612 and an outer portion 614. In some embodiments, the inner portion 612 and the outer portion 614 are made of different materials. In some embodiments, the inner portion 612 is a membrane made of a flexible material. In some embodiments, the flexible material is elastic. In some embodiments, the outer portion 614 is a frame made of plastic (e.g., hard plastic). However, other suitable materials can be used. In still another embodiment, the inner portion 612 and the outer portion 614 can be made of the same material.

The inner portion 612 can have a circular opening 616 that can fit over (e.g., engage) a portion of a prosthetic foot or prosthetic component (e.g., pylon), resulting in a substantially watertight connection between the inner portion 612 and the prosthetic foot. In some embodiments, the circular opening 616 can have an O-ring 618. In some embodiments, the opening 616 of the inner portion 612 fits over (e.g., engages) an adaptor of a prosthetic foot. In some embodiments, the opening 616 of the inner portion 612 fits around (e.g., engages) a shank of a prosthetic foot. In some embodiments, the opening 616 of the inner portion 612 engages a collar adaptor located on a prosthetic foot (e.g., the collar adaptor 700 shown in FIG. 31 and described below), the collar adaptor having a groove that can receive the O-ring 618 of the opening 616. In some embodiments, when the opening 616 is engaged with the corresponding portion of a prosthetic foot, the connection between the inner portion 612 and the prosthetic foot is substantially watertight.

In some embodiments, the outer portion 614 can have a top surface 620, a bottom surface 622, and an edge 624 defining a perimeter 626. The edge 624 and the top surface 620 form a corner 628 around the perimeter 626 of the outer portion 614, and, in some embodiments, this corner 628 is rounded off. In some embodiments, the top surface 620 is substantially flat. In some embodiments, the perimeter 626 has generally the shape of the ankle opening of a cosmetic cover for a prosthetic foot. The outer portion 614 can engage a cosmetic cover for a prosthetic foot. In some embodiments, the outer portion 614 can removably engage a cosmetic cover for a prosthetic foot. In some embodiments, the bottom surface 622 can engage a cosmetic cover for a prosthetic foot. In some embodiments the bottom surface 622 can have a first lip 630 and a second lip 640, wherein the first lip 630 is closer to the perimeter 626 of the outer portion 614 than the second lip 640, and whereby the two lips 630 and 640 define a cavity or slot 650 between them. In some embodiments, the first and second lips 630 and 640 can removably engage a cosmetic cover for a prosthetic foot.

In some embodiments, the first and second lips 630 and 640 are located generally near the perimeter 626 of the bottom surface 622. In some embodiments, the first lip 630 is a continuous projection that forms a single continuous ridge that runs generally parallel to the perimeter 626 of the outer portion 614. In some embodiments, the second lip 640 is a continuous projection that forms a single continuous ridge that runs generally parallel to the perimeter 626 of the outer portion 614. In some embodiments, the first and second lips 630 and 640 run generally parallel to the perimeter 626 of the outer portion 614. In some embodiments, the continuous first and second lips 630 and 640 define a cavity, slot or channel 650 that runs substantially parallel to the perimeter 626 of the outer portion 614 and that can removably receive at least a portion of a cosmetic cover for a prosthetic foot.

In some embodiments, the first lip 630 has an outer surface 632 and an inner surface 634. In some embodiments, the outer surface 632 of the first lip 630 is generally perpendicular to the top surface 620 of the outer portion 614. In some embodiments, the outer surface 632 is contiguous with the edge 624 of the outer portion 614 such that it is effectively a continuation of the edge 624 of the outer portion 614. In some embodiments, the inner surface 634 of the first lip 630 is at an angle relative to the outer surface 632 such that the first lip 630 becomes narrower as it moves away from the bottom surface 622 of the outer portion 614.

In some embodiments, the second lip 640 has an outer surface 642 and an inner surface 644. In some embodiments, the outer surface 642 of the second lip 640 is generally perpendicular to the top surface 620 of the outer portion 614. In some embodiments, the outer surface 642 of the second lip 640 is generally parallel to the outer surface 632 of the first lip 630. In some embodiments, the inner surface 644 of the second lip 640 has a semi-circle or round protrusion 646 on the portion of the surface 644 that is farthest away from the bottom surface 622 of the outer portion 614. In some embodiments, the portion of the inner surface 644 closest to the bottom surface 622 of the outer portion 614 is at an angle relative to the outer surface 642 of the second lip 640. In some embodiments, the semi-circle or round protrusion 646 on the inner surface 644 of the second lip 640 can removably engage a corresponding feature on a cosmetic cover for a prosthetic foot. In some embodiments, the second lip 640 can deflect towards first lip 630 during the process of engaging the seal cover to the cosmetic cover, and then return to the original un-deflected position to engage the cosmetic cover. In some embodiments, the connection between the outer portion 614 and the cosmetic cover is substantially watertight. In some embodiments, glue or epoxy may be used at the point of attachment to achieve a greater degree of waterproofing.

FIGS. 32-37 illustrate one embodiment of a seal cover 800 for a cosmetic cover for a prosthetic foot. In some embodiments, the seal cover 800 generally has the shape of the cross-section of a human ankle. In some embodiments, the seal cover 800 generally has the shape of the ankle opening of a cosmetic cover for a prosthetic foot. The seal cover 800 generally can have an inner portion 812 and an outer portion 814. In some embodiments, the inner portion 812 and the outer portion 814 are made of different materials. In some embodiments, the inner portion 812 is a membrane made of a flexible material. In some embodiments, the flexible material is elastic. In some embodiments, the outer portion 814 is a frame made of plastic (e.g., hard plastic). In still another embodiment, the inner portion 812 and the outer portion 814 can be made of the same material.

However, other suitable materials can be used. The inner portion 812 can have a circular opening 816 that can fit over (e.g., engage) a portion of a prosthetic foot or prosthetic component (e.g., pylon), resulting in a substantially watertight connection between the inner portion 812 and the prosthetic foot. In some embodiments, the circular opening 816 can have an O-ring 818. In some embodiments, the opening 816 of the inner portion 812 fits over (e.g., engages) an adaptor of a prosthetic foot. In some embodiments, the opening 816 of the inner portion 812 fits around (e.g., engages) a shank of a prosthetic foot. In some embodiments, the opening 816 of the inner portion 812 engages a collar adaptor located on a prosthetic foot (e.g., the collar adaptor 700 shown in FIG. 31 and described below), the collar adaptor having a groove that can receive the O-ring 818 of the opening 816. In some embodiments, the inner portion 812 can have excess material (e.g., be oversized) such that when the opening 816 is engaged with a portion of a prosthetic foot or prosthetic component, the inner portion 816 is not taut or rigid. In some embodiments, the excess material (or oversized configuration) of the inner portion 812 can define one or more folds 870 in the inner portion 812. In some embodiments, this excess material that defines one or more folds 870 allows for greater flexibility of the inner portion 812 when it is engaged with a prosthetic foot or prosthetic component. In some embodiments, when the opening 816 is engaged with the corresponding portion of a prosthetic foot, the connection between the inner portion 812 and the prosthetic foot is substantially watertight.

In some embodiments, the outer portion 814 can have a top surface 820, a bottom surface 822, and an edge 824 defining a perimeter 826. The edge 824 and the top surface 820 form a corner 828 around the perimeter 826 of the outer portion 814, and, in some embodiments, this corner 828 is rounded off. In some embodiments, the top surface 820 is substantially flat, though in other embodiments it can have other suitable configurations (e.g., curved, concave, convex). In some embodiments, the perimeter 826 has generally the shape of the ankle opening of a cosmetic cover 840 for a prosthetic foot 842. The outer portion 814 can engage a cosmetic cover 840 for a prosthetic foot 842. In some embodiments, the outer portion 814 can removably engage a cosmetic cover 840 for a prosthetic foot 842. In some embodiments, the bottom surface 822 can engage a cosmetic cover 840 for a prosthetic foot 842. In some embodiments, the outer portion 814 can engage a cosmetic cover 840 for a prosthetic foot 842 in the manner described and shown with respect to outer portion 514 and cosmetic cover 540 in FIGS. 21-25, via a series of protrusions 830 on the bottom surface 822 that can removably engage one or more complementary cavities, recesses or slots on the cosmetic cover 840. In some embodiments, the series of protrusions 830 on seal cover 800 is substantially similar to the series of protrusions 530 on seal cover 500 as described above for FIGS. 21-25. In some embodiments, the outer portion 814 can fit over or engage a cosmetic cover 840 for a prosthetic foot 842 in the manner described and shown with respect to outer portion 614 and in FIGS. 26-30, using a first and second lip to engage the cosmetic cover 840 (not shown for the embodiment of the seal cover 800). In some embodiments, the first and second lips (not shown) are substantially similar to the first lip 630 and second lip 640 on seal cover 600 described above for FIGS. 26-30.

Figure 37:
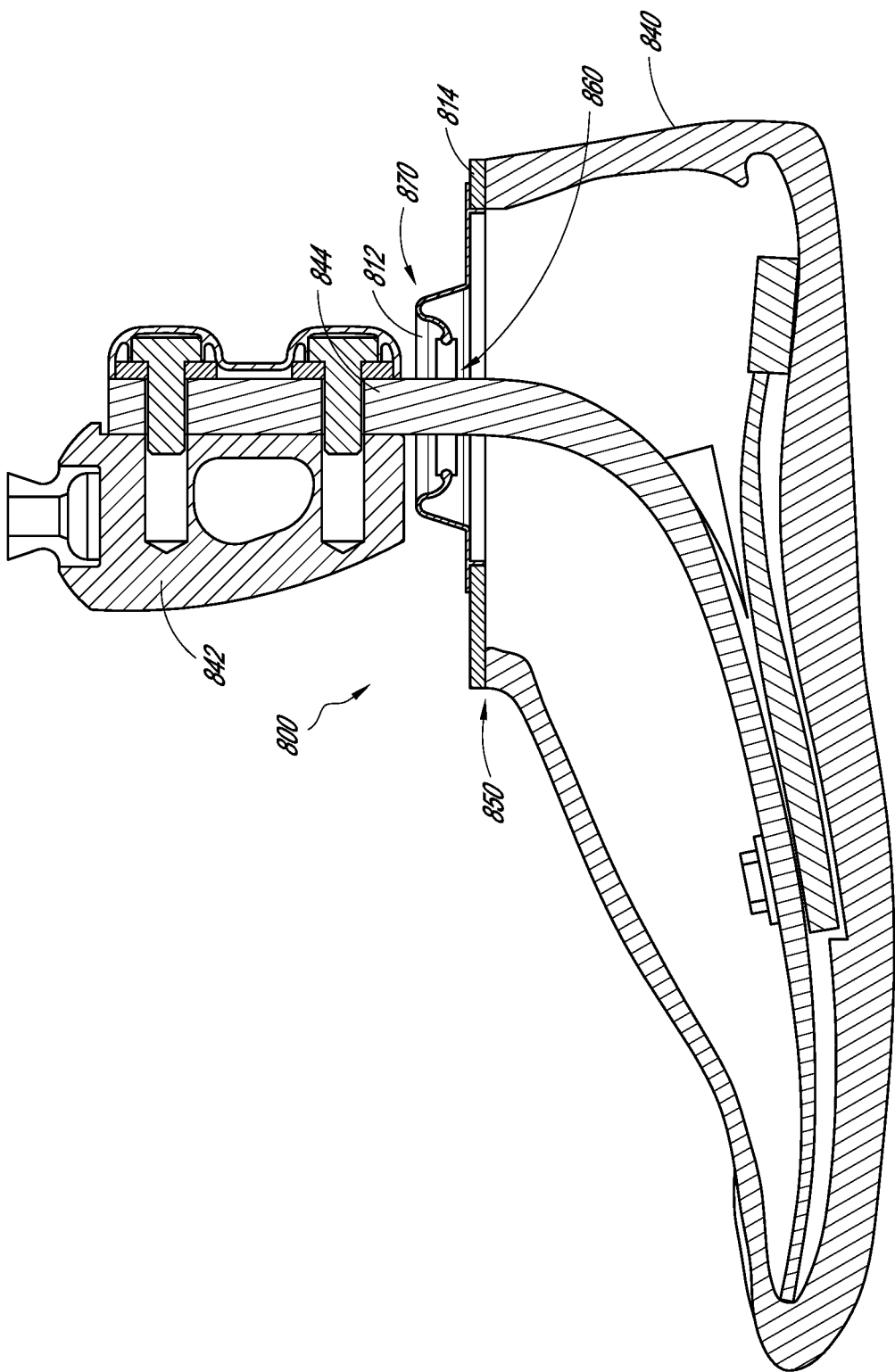
FIG. 37 is a cross-sectional view of one embodiment of the seal cover of FIG. 32 engaged with a cosmetic cover and a prosthetic foot system.

FIG. 37 illustrates one embodiment of a seal cover 800 engaged with a cosmetic cover 840 and fitted around (e.g., engaged with) a prosthetic foot system. In some embodiments, the outer portion 814 of the seal cover 800 is engaged with the cosmetic cover 840 such that the connection 850 between the outer portion 814 and the cosmetic cover 840 is substantially watertight. In some embodiments, the inner portion 812 of the seal cover 800 fits around (e.g., engages) a component, for example 842 or 844, of a prosthetic foot system such that the connection 860 between the inner portion 812 and the prosthetic foot system is substantially watertight. In some embodiments, the inner portion 812 of the seal cover 800 fits around (e.g., engages) a collar adaptor (e.g., the collar adaptor 700 shown in FIG. 31 and described below) located on or around a component of a prosthetic foot system, wherein the collar adaptor can have a groove to receive the inner portion 812. In some embodiments, the inner portion 812 has excess material (or is oversized) resulting in at least one fold 870, wherein the at least one fold 870 allows for greater flexibility in the inner portion 812 and the connection 860 between the inner portion 812 and the prosthetic foot system. In some embodiments, the inner portion 812 can have varying shapes or designs, including one or more folds 870.

Figure 31:
FIG. 31 is a partial side, top and front profile view of one embodiment of a collar adaptor.
Figure 32:
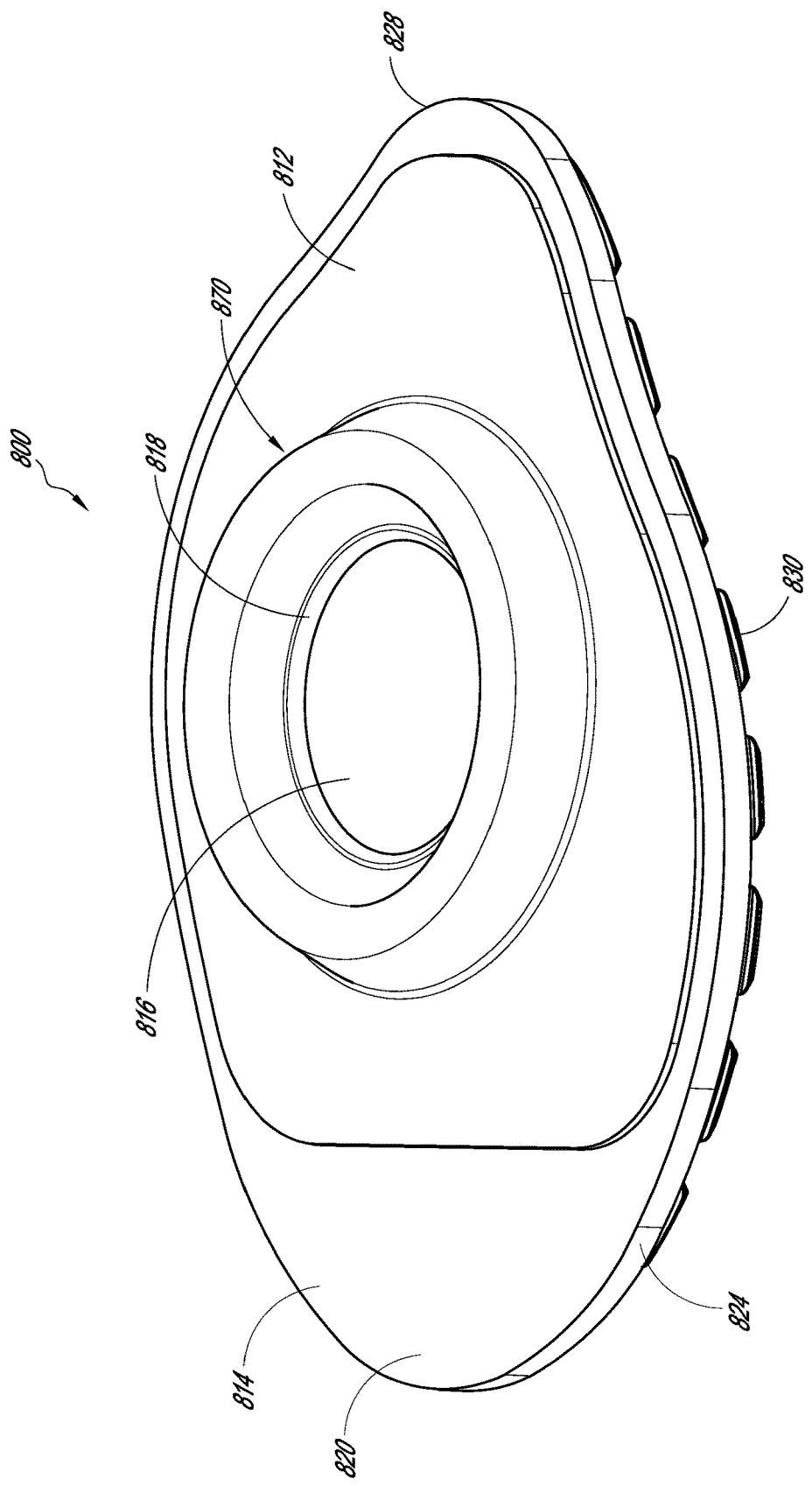
FIG. 32 is a partial side, top and front profile view of one embodiment of a seal cover for a prosthetic foot.
Figure 33:
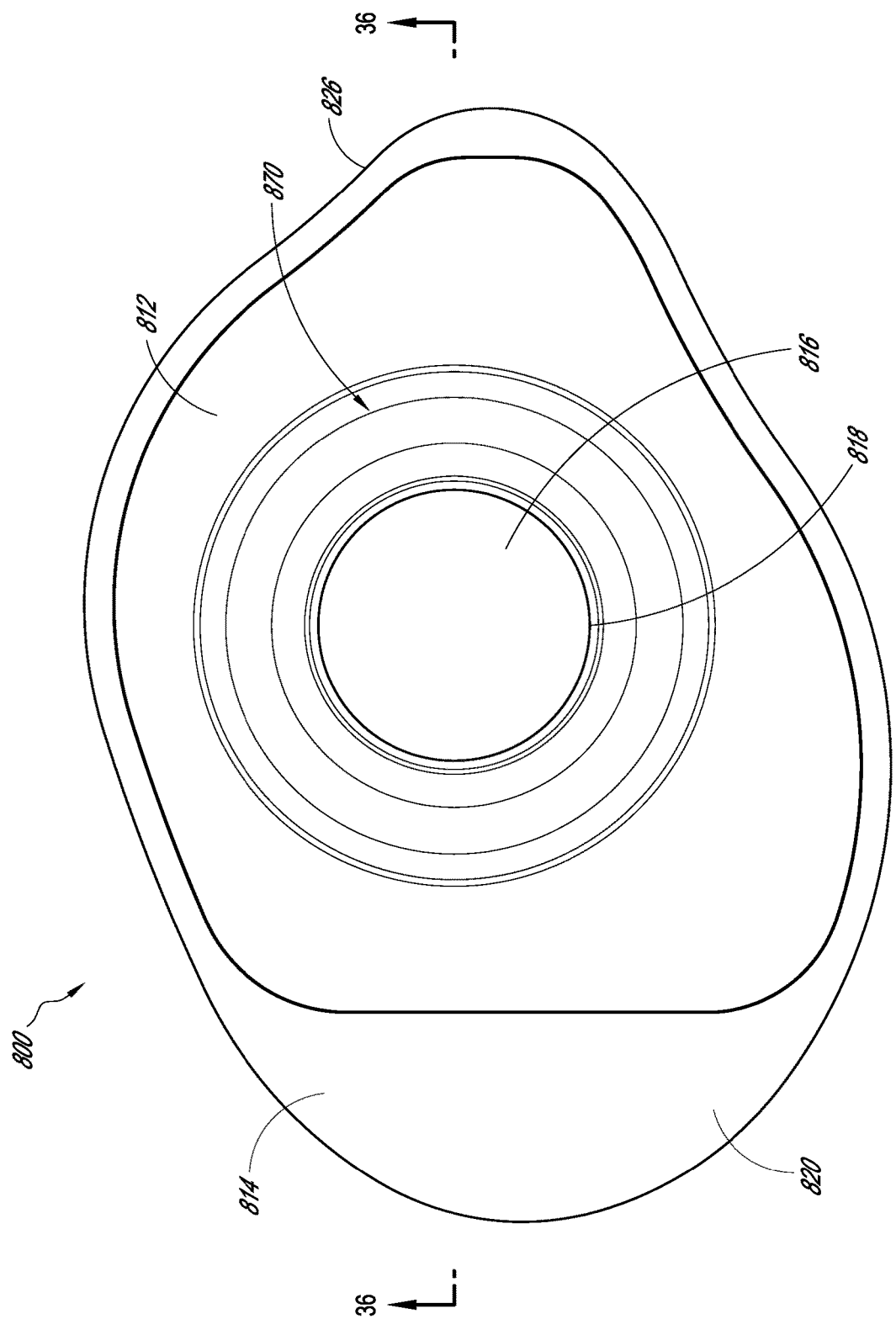
FIG. 33 is a top plan view of the seal cover of FIG. 32.
Figure 34:
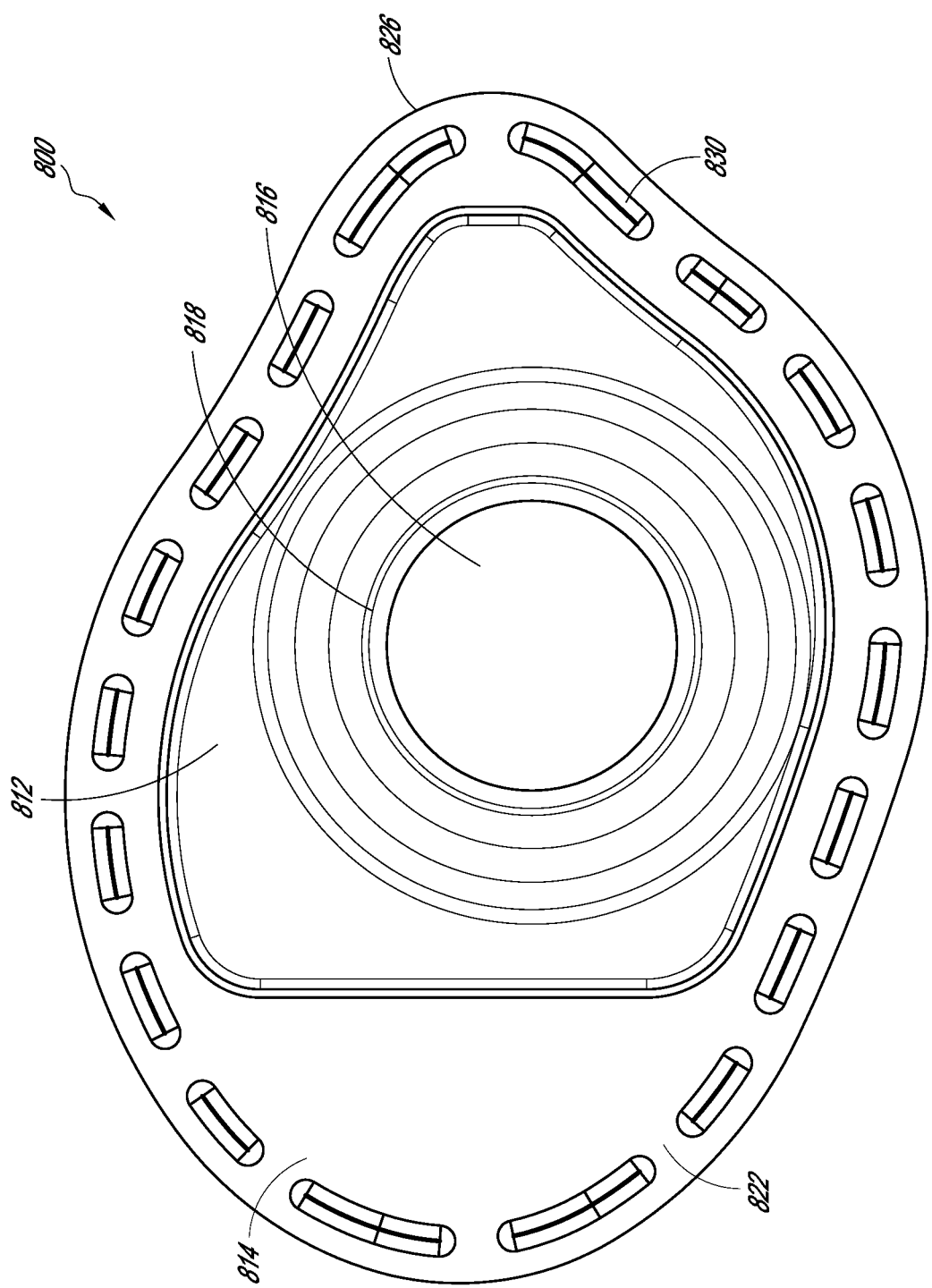
FIG. 34 is a bottom plan view of the seal cover of FIG. 32.
Figure 35:
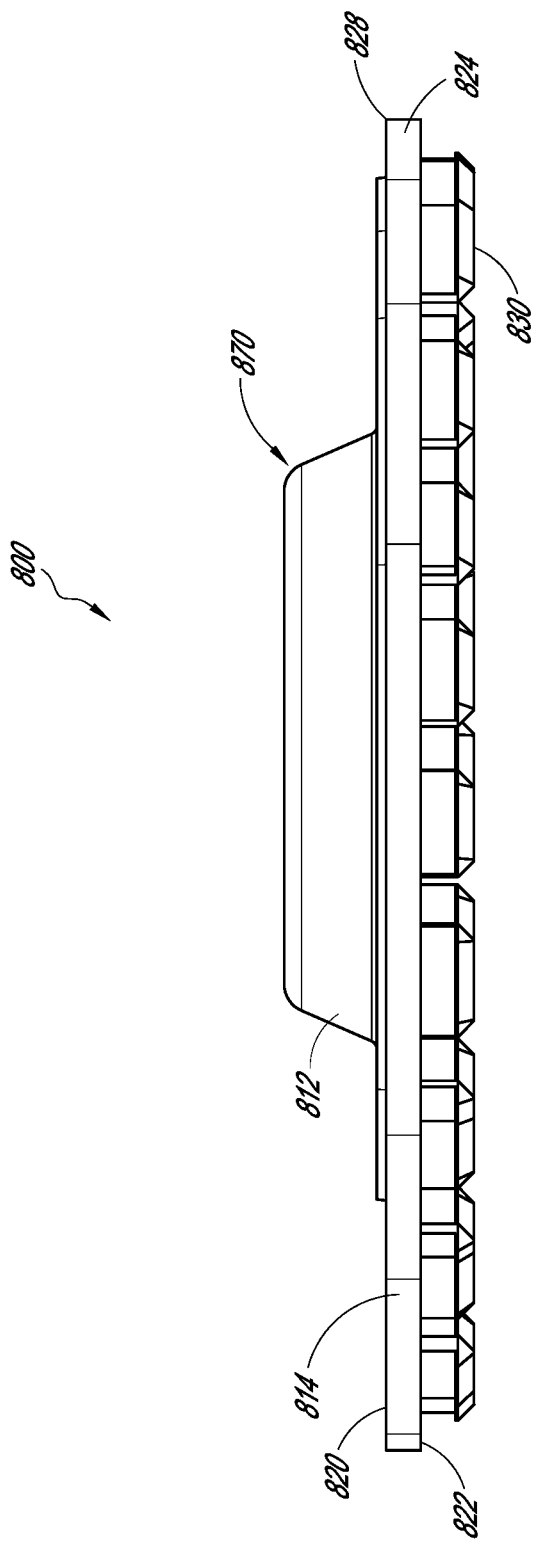
FIG. 35 is a side profile view of the seal cover of FIG. 32.
Figure 36:
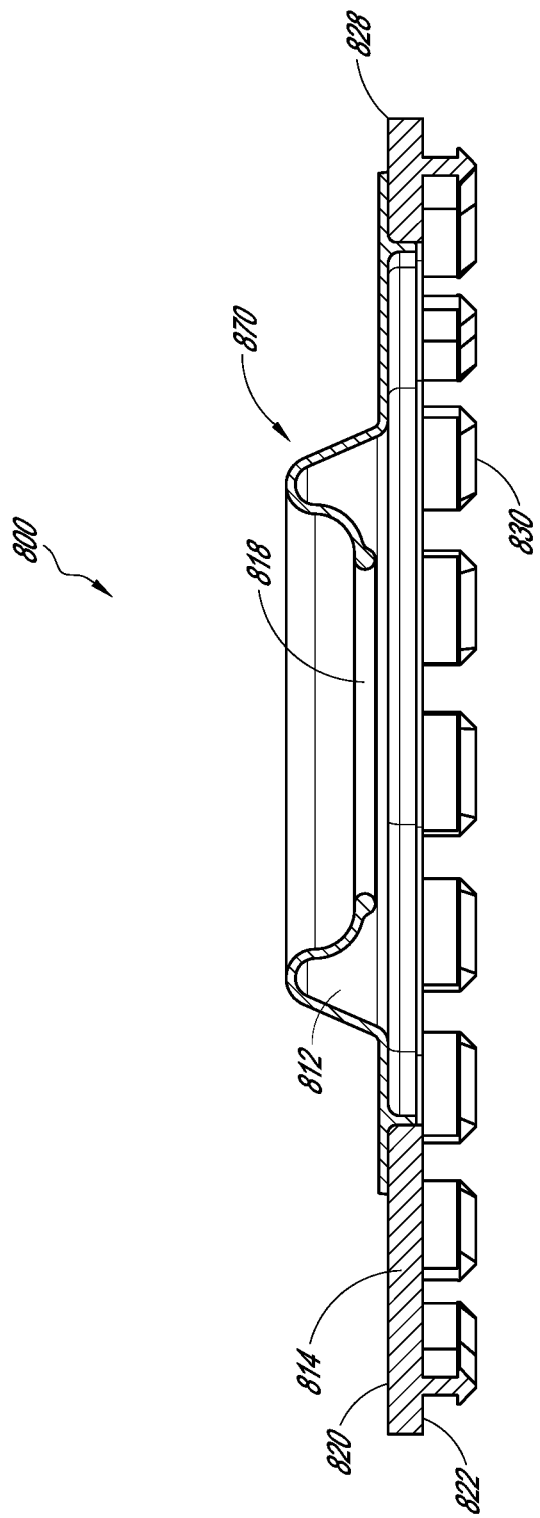
FIG. 36 is a cross-sectional view of the seal cover of FIG. 32, as viewed along plane 36-36 in FIG. 33.

FIG. 31 illustrates one embodiment of a collar adaptor 700 for a prosthetic foot system that can receive (e.g., engage) a seal cover, such as the seal cover 500 or seal cover 600. In some embodiments, the collar adaptor 700 can have a groove 710 that can receive (e.g., engage) at least a portion of a seal cover. In some embodiments, the groove 710 can receive (e.g., engage) an inner portion of a seal cover. In some embodiments, the groove 710 can receive (e.g., engage) an O-ring of an inner portion of a seal cover. In some embodiments, the groove 710 is circumferential. In some embodiments, the groove 710 can have a semi-circular cross-section. In some embodiments, the collar adaptor 700 can receive (e.g., engage) at least a portion of a seal cover such that the connection between the collar adaptor 700 and the seal cover is substantially watertight.

In some embodiments, the collar adaptor 700 can fit on, over, or around (e.g., engage) a portion or component of a prosthetic foot system, such as a proximal portion of a foot plate of the prosthetic foot or a pylon attached to the prosthetic foot. In some embodiments, the collar adaptor 700 can fit on, over, or around (e.g., engage) a portion or component of a prosthetic foot system via an aperture in the collar adaptor 700. In some embodiments, the aperture can have a substantially rectangular shape. In some embodiments, the aperture can have a substantially circular shape. In some embodiments, the aperture can have a shape such that the collar adaptor 700 can fit on, over, or around a portion or component of a prosthetic foot system (e.g., the shape of the aperture generally coincides with a cross-sectional shape of the component to which the adaptor is coupled). In some embodiments, the collar adaptor 700 can fit on, over, or around (e.g., engage) the shank, pylon, pyramid adaptor, foot plate, or any other portion or component of a prosthetic foot system. In some embodiments, the collar adaptor 700 can fit on, over, or around (e.g., engage) at least a portion or component of a prosthetic foot system such that the connection between the collar adaptor 700 and the at least a portion of the prosthetic foot system is substantially watertight. In some embodiments, the collar adaptor 700 can fit on, over, or around (e.g., engage) a portion or component of a prosthetic foot system and can removably receive (e.g., engage) at least a portion (i.e., an inner portion or O-ring) of a seal cover resulting in a substantially watertight connection between the prosthetic foot system and the seal cover. In some embodiments, the collar adaptor 700 can be integrated into (e.g., manufactured as a part of) at least a portion of a prosthetic foot system, such that the portion of the prosthetic foot system can have a groove 710 that can receive (e.g., engage) a portion of a seal cover.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot, comprising:

an elongate foot member consisting of a single foot plate and having a toe end, an ankle end, and a length extending from the toe end to the ankle end, the elongate foot member further having a medial side surface, a lateral side surface, and a width extending from the medial side surface to the lateral side surface;

a toe attachment removably coupled solely to the toe end of the elongate foot member and having a top surface, a bottom surface, a distal end, a substantially uniform thickness between the top surface and the bottom surface, a proximal end, the toe attachment defining a slot therein and having a length shorter than a length of the elongate foot member, the toe attachment having only a single cavity that extends from an opening on a surface at the proximal end toward the distal end of the toe attachment, the single cavity receiving the toe end of the elongate foot member, wherein the opening is generally rectangular with a width greater than a height, the width of the opening being greater than the width of the elongate foot member, the cavity being defined by a substantially planar top wall and a substantially planar bottom wall; and a foot cover that receives the assembled elongate foot member from the toe end to the ankle end and toe attachment in a cavity of the foot cover, the toe attachment facilitating the fitting of the elongate foot member in the foot cover, wherein the slot in the toe attachment extends from the top surface to the bottom surface defining a medial lobe and a lateral lobe of the toe attachment, the slot configured to removably receive a strap of a sandal when said sandal is coupled to the prosthetic foot.

2. The prosthetic foot of claim 1, wherein the slot is generally U-shaped.

3. The prosthetic foot of claim 1, wherein the toe attachment is attachable to at least a distal toe surface and the medial and lateral side surfaces of the elongate foot member to alter a shape of the prosthetic foot by increasing a least one of a width and a length of at least a portion of the elongate foot member.

4. The prosthetic foot of claim 1, wherein the medial lobe and the lateral lobe of the toe attachment have different widths.

5. The prosthetic foot of claim 1, wherein the top surface and the bottom surface of the toe attachment curve upwardly away from the proximal end of the toe attachment.

* * * * *